(12) United States Patent
Vallapureddy et al.

(10) Patent No.: US 7,743,151 B2
(45) Date of Patent: Jun. 22, 2010

(54) SYSTEM AND METHOD FOR PROVIDING DIGITAL DATA COMMUNICATIONS OVER A WIRELESS INTRA-BODY NETWORK

(75) Inventors: Vineel Vallapureddy, St. Paul, MN (US); Cynthia Morrissey, St. Paul, MN (US); Paul Holmquist, Andover, MN (US); Abhi Chavan, Maple Grove, MN (US); Jeffrey A. Von Arx, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1182 days.

(21) Appl. No.: 10/913,118

(22) Filed: Aug. 5, 2004

(65) Prior Publication Data

US 2006/0031378 A1 Feb. 9, 2006

(51) Int. Cl.
*G06F 15/16* (2006.01)
*A61N 1/00* (2006.01)
*G08C 19/16* (2006.01)
*G08B 1/08* (2006.01)

(52) U.S. Cl. .................. 709/227; 709/208; 607/32; 128/903; 340/870.01; 340/539.12

(58) Field of Classification Search ............ 709/208, 709/224; 607/9, 32; 455/343.2; 370/312; 702/120; 340/539.12, 870.01
See application file for complete search history.

(56) References Cited

U.S. PATENT DOCUMENTS 5,539,775 A * 7/1996 Tuttle et al. .................. 375/145
5,814,089 A * 9/1998 Stokes et al. ................. 607/32
6,024,699 A * 2/2000 Surwit et al. ................ 600/300
6,083,248 A * 7/2000 Thompson .................... 607/30
6,141,588 A * 10/2000 Cox et al. ...................... 607/9
6,171,256 B1 * 1/2001 Joo et al. .................... 600/508
6,223,018 B1 * 4/2001 Fukumoto et al. .......... 455/41.1
6,336,903 B1 1/2002 Bardy (Continued)

FOREIGN PATENT DOCUMENTS

WO WO-9843700 8/1998

OTHER PUBLICATIONS

W. Diffie, "The First Ten Years Of Public-Key Cryptography," Proceedings of the IEEE, vol. 76, No. 5, pp. 560-577 (May 1988).

(Continued)

*Primary Examiner*—Joseph Thomas
*Assistant Examiner*—Tae K Kim
(74) *Attorney, Agent, or Firm*—Pauly, DeVries, Smith & Deffner, L.L.C.

(57) ABSTRACT

A system and method for providing digital data communications over a wireless intra-body network is presented. A physical protocol layer is logically defined with an identifier uniquely assigned to a plurality of implantable devices in an intra-body network. Functions are specified within the physical protocol layer to transact data exchange over a wireless interface. A slave implantable device is activated in response to an activation signal transmitted through the wireless interface by a master implantable device. A wireless communications link is established between the slave implantable device and the master implantable device upon matching of the identifier assigned to the slave implantable device. Data is communicated intra-bodily over the communications link.

45 Claims, 16 Drawing Sheets

U.S. PATENT DOCUMENTS

| | | | |
|---|---|---|---|
| 6,363,282 B1 | 3/2002 | Nichols et al. | |
| 6,368,284 B1 | 4/2002 | Bardy | |
| 6,398,728 B1 | 6/2002 | Bardy | |
| 6,411,840 B1 | 6/2002 | Bardy | |
| 6,416,471 B1* | 7/2002 | Kumar et al. | 600/300 |
| 6,440,066 B1 | 8/2002 | Bardy | |
| 6,827,670 B1* | 12/2004 | Stark et al. | 482/9 |
| 6,897,788 B2* | 5/2005 | Khair et al. | 340/870.16 |
| 6,968,375 B1* | 11/2005 | Brown | 709/224 |
| 6,993,393 B2 | 1/2006 | Von Arx et al. | 607/60 |
| 7,024,249 B2 | 4/2006 | Weisner et al. | 607/60 |
| 7,103,344 B2* | 9/2006 | Menard | 455/343.2 |
| 7,103,578 B2* | 9/2006 | Beck et al. | 705/75 |
| 7,171,166 B2* | 1/2007 | Ng et al. | 455/73 |
| 7,218,969 B2* | 5/2007 | Vallapureddy et al. | 607/60 |
| 7,257,447 B2* | 8/2007 | Cates et al. | 607/59 |
| 7,260,436 B2* | 8/2007 | Kilgore et al. | 607/60 |
| 7,285,090 B2* | 10/2007 | Stivoric et al. | 600/300 |
| 7,324,850 B2* | 1/2008 | Persen et al. | 607/30 |
| 7,392,092 B2* | 6/2008 | Li et al. | 607/60 |
| 2002/0077673 A1* | 6/2002 | Penner et al. | 607/60 |
| 2002/0177782 A1* | 11/2002 | Penner | 600/485 |
| 2002/0183956 A1* | 12/2002 | Nightingale | 702/120 |
| 2003/0114897 A1* | 6/2003 | Von Arx et al. | 607/60 |
| 2004/0103001 A1* | 5/2004 | Mazar et al. | 705/2 |
| 2005/0138428 A1* | 6/2005 | McAllen et al. | 713/201 |
| 2005/0203389 A1* | 9/2005 | Williams | 600/431 |
| 2005/0288736 A1* | 12/2005 | Persen et al. | 607/60 |
| 2006/0009818 A1* | 1/2006 | Von Arx et al. | 607/60 |
| 2006/0056325 A1* | 3/2006 | Wood, Jr. | 370/312 |

OTHER PUBLICATIONS

Medtronic, Inc., "Research Presented at ADA Annual Meeting Demonstrates Accuracy and Feasibility of Artificial Pancreas Components," News Release, http://www.medtronic.com/newsroom/news_20020617b.htmi (Jun. 17, 2002), 3 pages.

International Search Report and Written Opinion for PCT/US20051027646 (corresponding to U.S. Appl. No. 101913,118), mailing date Jan. 24, 2006, 16 pages.

Office Action from the European Patent Office in EP Application No. 05782998.8 (corresponding to U.S. Appl. No. 101913,118), received Jan. 28, 2008, 4 pages.

Response to Office Action in EP Application No. 05782998.8 (corresponding to U.S. Appl. No. 10/913,118), dated Feb. 12, 2008, 15 pages.

Office Action from the European Patent Office in EP Application No. 05782998.8 (corresponding to U.S. Appl. No. 101913,118), received Aug. 29, 2008, 3 pages.

Response to Office Action in EP Application No. 05782998.8 (corresponding to U.S. Appl. No. 10/913,118), dated Feb. 27, 2009, 10 pages.

* cited by examiner

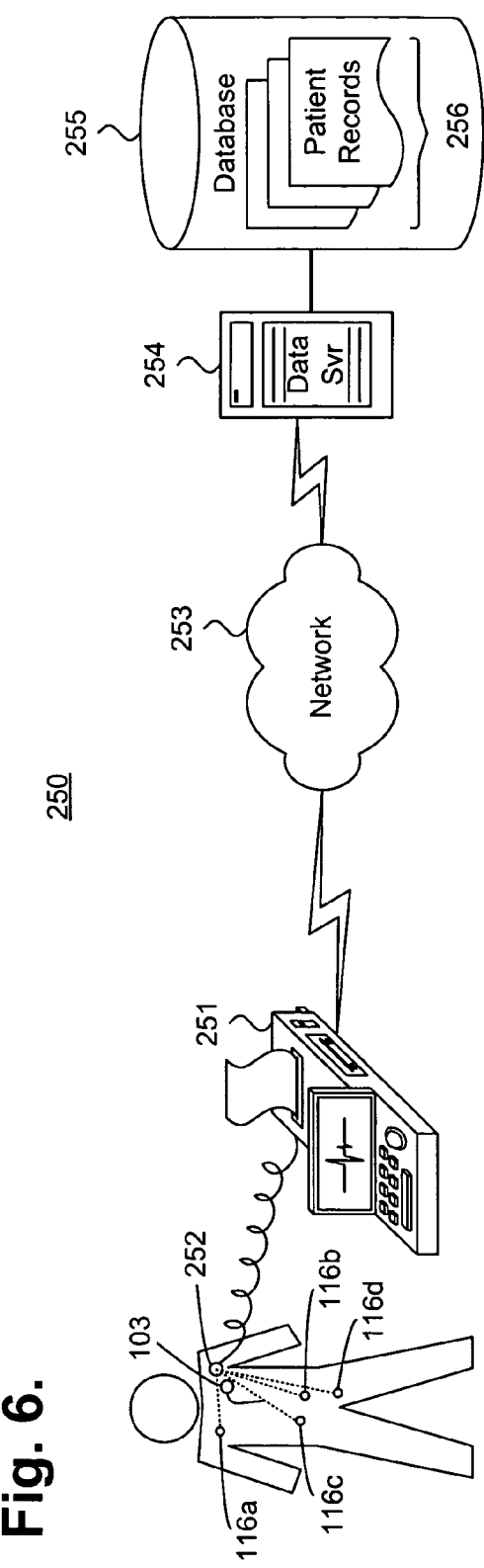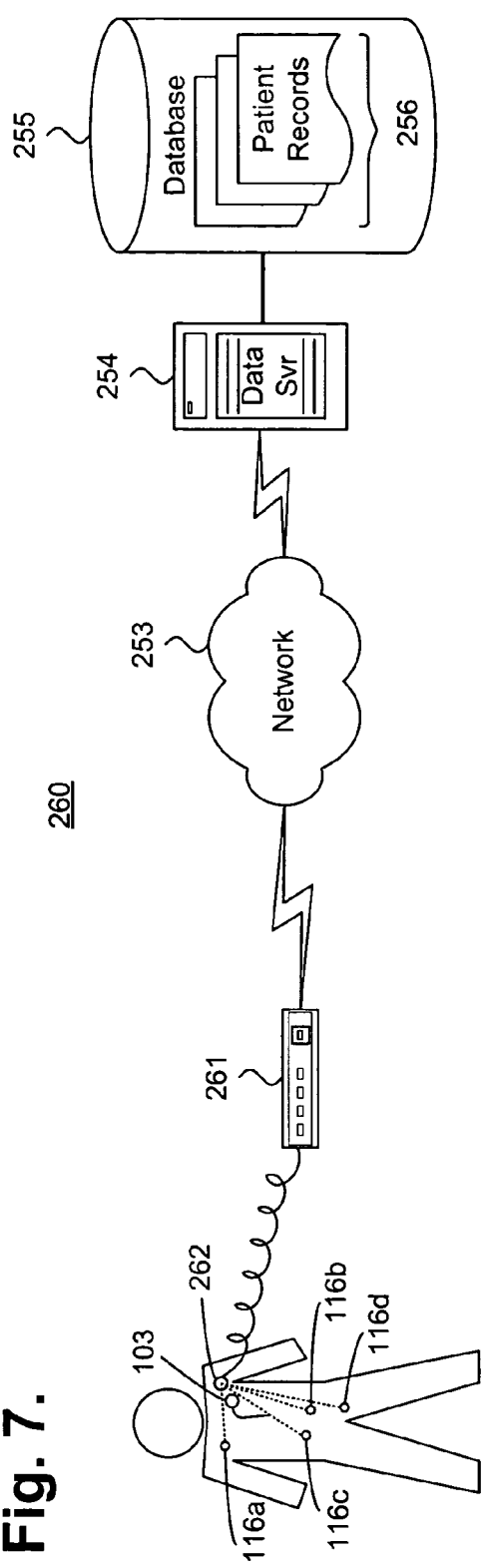
Fig. 6.
Fig. 7.

SYSTEM AND METHOD FOR PROVIDING DIGITAL DATA COMMUNICATIONS OVER A WIRELESS INTRA-BODY NETWORK

FIELD OF THE INVENTION

The invention relates in general to digital data communications and, specifically, to a system and method for providing digital data communications over a wireless intra-body network.

BACKGROUND OF THE INVENTION

In general, implantable medical devices (IMDs) provide in situ therapy delivery, such as cardiac resynchronization, defibrillation, neural stimulation and drug delivery, and physiological monitoring and data collection. Once implanted, IMDs function autonomously by relying on pre-programmed operation and control over therapeutic and monitoring functions. As necessary, IMDs can be interfaced to external devices, such as programmers, repeaters and similar devices, which can program, troubleshoot, recharge and exchange parametric and physiological data, typically through induction or similar forms of near-field telemetry.

Typically, therapy delivery and physiological data monitoring and collection are performed in conjunction with a closed-feedback loop that includes one or more sensors provided with each IMD. For example, sensors included on the distal end of electrode leads of an implantable cardiac defibrillator (ICD) can monitor intracardiac electrical activity preceding and subsequent to therapy delivery. However, the feedback is limited only to the activity sensed within the intracardiac area immediate to each sensor and such feedback may be insufficient to determine whether the therapy was effective. Moreover, additional physiological parameters that might be helpful in ascertaining therapy efficacy, such as blood pressure, chemistry or body temperature, remain unavailable to the ICD due to the limited functionality provided by the local electrode lead sensors.

Certain IMDs can be supplemented with additional implantable sensors to monitor physiological data in other locations of a patient's body, such as described in Medtronic, Inc., "Research Presented at ADA Annual Meeting Demonstrates Accuracy and Feasibility of Artificial Pancreas Components," News Release, http://www.medtronic.com/newsroom/news_20020617b.html (Jul. 17, 2002), the disclosure of which is incorporated by reference. Currently, such sensors can interface to an IMD through a wired interconnection or can operate autonomously. Neither approach provides a satisfactory solution. Wired interconnections are highly invasive, potentially requiring an intra-body tunnel to channel interconnect wires. Such intra-body tunneling exposes the patient to possible adverse side effects, including injury to internal tissue and organs, infection and discomfort. In addition, coordinating communications with the IMD becomes increasingly complex with the addition of each additional wired sensor, which also requires an interconnection interface and dedicated set of interconnect wires.

Autonomous operation avoids the side effects of wired interconnections and instead relies upon the external download of stored physiological data. External data download can be critical, as most implantable sensors have limited on-board storage, often only available for storing episodic data observed over a recent time period. Externally downloaded physiological data, though, can only be made available to the IMD indirectly by relay through an external device. As a result, the downloaded physiological data is untimely and of less use than real time physiological data received directly from each implantable sensor.

For example, U.S. Pat. No. 7,024,248, issued on Apr. 4, 2006, and U.S. Pat. No. 7,273,457, issued on Sep. 25, 2007, both describe an implantable sensor interfaceable via an external acoustic transducer. The sensor functions autonomously to monitor pressure or physiological parameters. The acoustic transducer transmits acoustic signals into a patient's body to interface with the implantable sensor, which downloads pressure measures recorded by the sensor. Each individual sensor is a stand-alone device and is not configurable into a network arrangement allowing direct communication between implantable sensors and IMDs.

Therefore, there is a need for an approach to providing non-wired interconnectivity between a plurality of implantable devices, including one or more IMDs and one or more implantable modules and preferably supporting configuration as a master-to-slave or peer-to-peer network configuration.

There is a further need for an approach to providing a network communications protocol facilitating the data exchange between wireless modules within an intra-body digital data communications network, preferably providing both physical and application layers to support a plurality of application types.

There is a further need for an approach to providing flexible external interfaces between a plurality of external devices and implantable modules configured into an intra-body digital data communications network. Preferably, such an approach would support communication with a programmer, repeater or special purpose device, such as a recharger, through high efficiency interfaces.

SUMMARY OF THE INVENTION

The invention includes a system and method for exchanging data between devices implantable within a biological body, such as a human body, via an intra-body digital data network. Each implantable device and, in a further embodiment, each external device, implement a hierarchical network protocol stack defined into a physical layer, specifying physical interfacing between devices and can include one or more application-specific layers, handling details for particular applications. In a further embodiment, the network protocol stack can also include one or more intermediate layers specifying packet structure and routing, such as data link, network and transport layers, between the physical layer and the application-specific layers and an application layer. In one embodiment, digital data is exchanged within the intra-body network through an acoustic carrier signal, although other forms of carrier signals are possible. In a further embodiment, the implantable modules interface to an external device, such as a programmer, repeater or similar device, to perform programming, troubleshooting, recharging and to exchange parametric and physiological data.

In one embodiment, one or more implantable modules interface directly with at least one implantable medical device in a master-slave network configuration. The implantable medical device, such as a pacemaker, ICD or similar device, functions as a master module that initiates and controls communications with one or more implantable modules, such as dedicated therapy delivery or sensor devices, that serve as slave modules. To initiate a communications session, the master module sends an activation signal to awaken the slave modules into a high power listening mode. The master module subsequently sends a wireless request to one or more of the slave modules to execute a command message. Upon completion, the slave modules send the command execution results to the master module in a wireless data packet and return to a low power listening mode.

In a further embodiment, the implantable modules are configured in a peer-to-peer network configuration with control over communications distributed amongst the individual implantable modules. An implantable module, which can include an implantable medical device, functions as a requesting peer that communicates directly with one or more other implantable modules that serve as responding peers. Communications sessions are periodically self-initiated between the cooperating implantable modules, which exchange command message requests and results through wireless data packets.

One embodiment provides a system and method for providing digital data communications over a wireless intra-body network. A physical protocol layer is logically defined with an identifier uniquely assigned to a plurality of implantable devices in an intra-body network. Functions are specified within the physical protocol layer to transact data exchange over a wireless interface. A slave implantable device is activated in response to an activation signal transmitted through the wireless interface by a master implantable device. A wireless communications link is established between the slave implantable device and the master implantable device upon matching of the identifier assigned to the slave implantable device. Data is communicated intra-bodily over the communications link.

A further embodiment provides a system and method for providing digital data communications over a wireless intra-body network. A physical protocol layer is logically defined with an identifier uniquely assigned to a plurality of peer implantable devices in an intra-body network. Functions are specified within the physical protocol layer to transact data exchange over a wireless interface. A wireless communications link is established between a responding peer implantable device and a requesting peer implantable device upon matching of the identifier assigned to the responding peer implantable device. Data is communicated intra-bodily over the communications link A further embodiment provides a system and method for providing digital data communications over a wireless intra-body network. A physical protocol layer is logically defined with an identifier uniquely assigned to a plurality of implantable devices in an intra-body network and an identifier uniquely assigned to a device external to the intra-body network. Functions are specified within the physical protocol layer to transact data exchange over a wireless interface. An implantable device is activated in response to an activation signal transmitted through the wireless interface by the external device. A wireless communications link is established between the implantable device and the external device upon matching of the identifier assigned to the slave implantable device. Data is communicated intra-bodily over the communications link.

Still other embodiments of the invention will become readily apparent to those skilled in the art from the following detailed description, wherein are described embodiments of the invention by way of illustrating the best mode contemplated for carrying out the invention. As will be realized, the invention is capable of other and different embodiments and its several details are capable of modifications in various obvious respects, all without departing from the spirit and the scope of the invention. Accordingly, the drawings and detailed description are to be regarded as illustrative in nature and not as restrictive.

BRIEF DESCRIPTION OF THE DRAWINGS

FIG. 6 is a functional block diagram showing, by way of example, a programmer-based external interface with a wireless intra-body network.

FIG. 7 is a functional block diagram showing, by way of example, a repeater-based external interface with a wireless intra-body network.

DETAILED DESCRIPTION

System Overview

Figure 1:
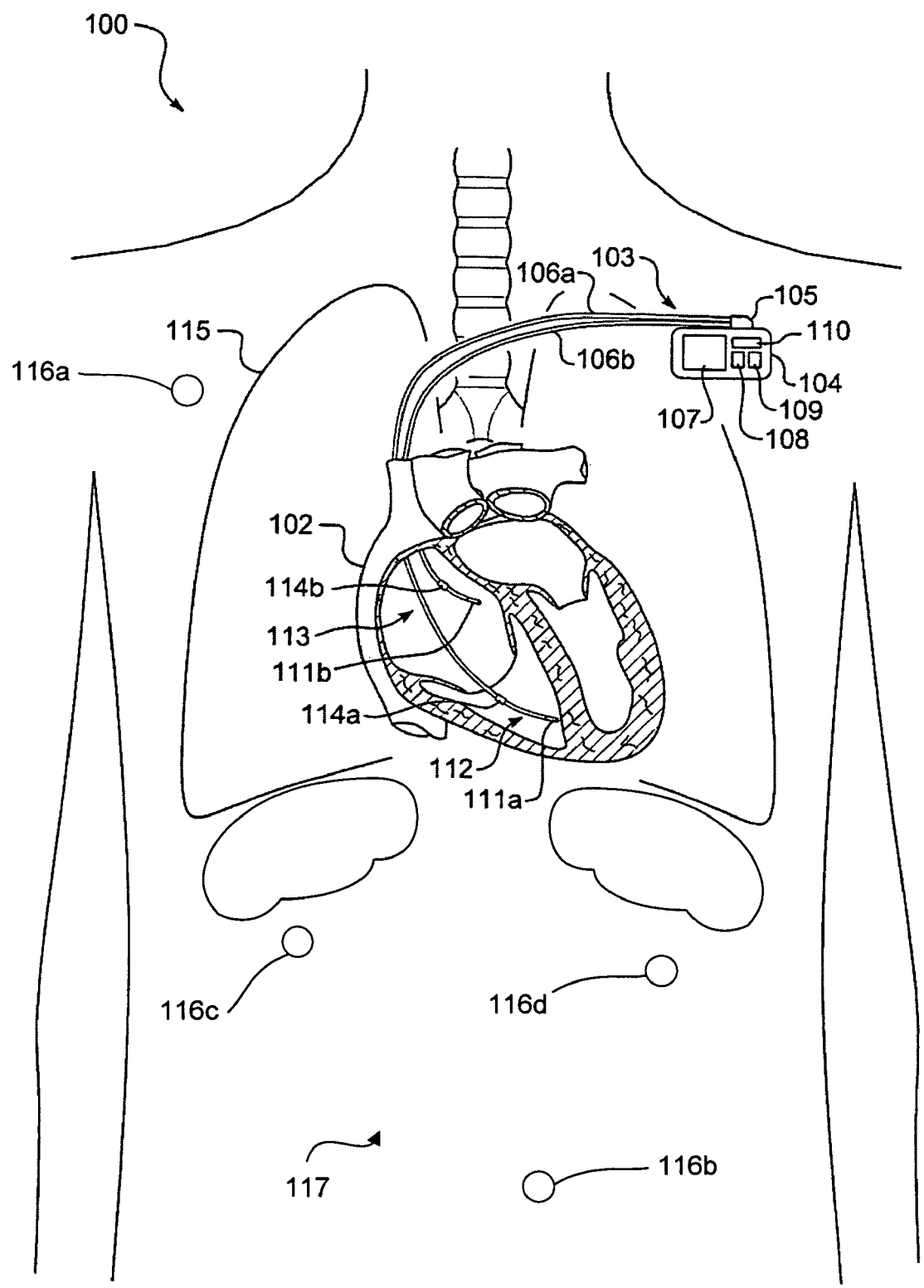
FIG. 1 is a block diagram showing a system for providing digital data communications over a wireless intra-body network, in accordance with an embodiment of the invention.

FIG. 1 is a block diagram 100 showing a system for providing digital data communications over a wireless intra-body network 117, in accordance with an embodiment of the invention. By way of example, an implantable medical device (IMD) 103, such as a pacemaker, implantable cardiac defibrillator (ICD) or similar device, is surgically implanted in the chest or abdomen of a patient. In addition, one or more implantable modules (IMs) 116a-d are surgically implanted in the chest, abdomen, or other bodily locations of the patient. Each IM 116a performs an autonomous therapeutic or sensing function, as further described below with reference to FIG. 9.

The IMD 103 and IMs 116a-d together form an intra-body network 117, which are configured into an interconnected network topology to facilitate wireless digital data exchange. In one embodiment, one or more IMDs 103 interface directly with at least one IM 116a-d in a master-slave network configuration, as further described below with reference to FIGS. 2A-B. In a further embodiment, one or more external devices interface directly with at least one IMD 103 or IM 116a. In a still further embodiment, one or more IMDs 103 can participate as slave implantable devices. The master-slave network configuration assigns the bulk of the processing and communications burden on devices that have greater processing and power capacities, such as the IMD 103, while attempting to conserve energy on more resource-limited devices, such as the IMs 116a-d. Communications can be exchanged between the master implantable device and one or more slave implantable devices in a one-to-one or one-to-many relationship.

In a further embodiment, the IMs 116a-d are configured in a peer-to-peer network configuration with control over communications distributed amongst the individual IMs 116a-d, as further described below with reference to FIGS. 3A-B. In a still further embodiment, the peer-to-peer network configuration can also include one or more IMDs 103. The peer-to-peer network configuration enables all implantable devices, including IMDs 103 and IMs 116a-d, to communicate directly with each other. Communications can be exchanged between peer implantable devices in a one-to-one or one-to-many relationship.

Other network configurations, topologies and arbitration schemes are also possible. For example, the IMD 103 and IMs 116a-d can be structured in a hierarchical network configuration or as a series of subnetworks. In addition, arbitration between competing implantable devices can be performed through various carrier accessing means, including carrier sensing, multiple access with collision avoidance (CSMA-CA); carrier sensing, multiple access with collision detection (CSMA-CD); and token exchange.

By way of example, an IMD 103 for providing cardiac resynchronization therapy is described. The IMD 103 includes a housing 104 and terminal block 105 coupled to a set of leads 106a-b. During surgery, the leads 106a-b are threaded through a vein and placed into the heart 102 with the distal tips of each lead 106a-b positioned in direct contact with heart tissue. The IMD housing 104 contains a battery 107, control circuitry 108, memory 109, and telemetry circuitry 110. The battery 107 provides a finite power source for the IMD components. The control circuitry 108 samples and processes raw data signals and includes signal filters and amplifiers, memory and a microprocessor-based controller. The memory 109 includes a memory store in which raw physiological signals can be stored for later retrieval and analysis by an external device, such as a programmer, repeater or similar device. The telemetry circuitry 110 provides an interface between the IMD 103 and the IMs 116a-d, as further described below beginning with reference to FIG. 10, and between the IMD 103 and an external device, such as a programmer, repeater or similar device, as further described below with reference to FIGS. 6-8. For external devices, the telemetry circuitry 110 enables operating parameters to be non-invasively programmed into the memory 109 and can allow patient information collected and transiently stored in the memory 109 to be sent to the external device for further processing and analysis.

The IMD 103 is in direct electrical communication with the heart 102 through electrodes 111a-b positioned on the distal tips of each lead 106a-b. By way of example, the set of leads 106a-b can include a right ventricular electrode 111a, preferably placed in the right ventricular apex 112 of the heart 102, and a right atrial electrode 111b, preferably placed in the right atrial chamber 113 of the heart 102. The set of leads 106a-b can also include a right ventricular electrode 114a and a right atrial electrode 114b to enable the IMD 103 to directly collect raw physiological measures, preferably through millivolt measurements. Other configurations and arrangements of leads and electrodes can also be used. Furthermore, although described with reference to IMDs for providing cardiac monitoring and therapy delivery, suitable IMDs also include other types of implantable therapeutic and monitoring devices in addition to or in lieu of cardiac monitoring and therapy delivery IMDs, including IMDs for providing neural stimulation, drug delivery, and physiological monitoring and collection, as well as IMDs primarily dedicated to communicating with other implantable modules within an intra-body network 117.

Master-Slave Intra-Body Network Configuration

Figure 2A:
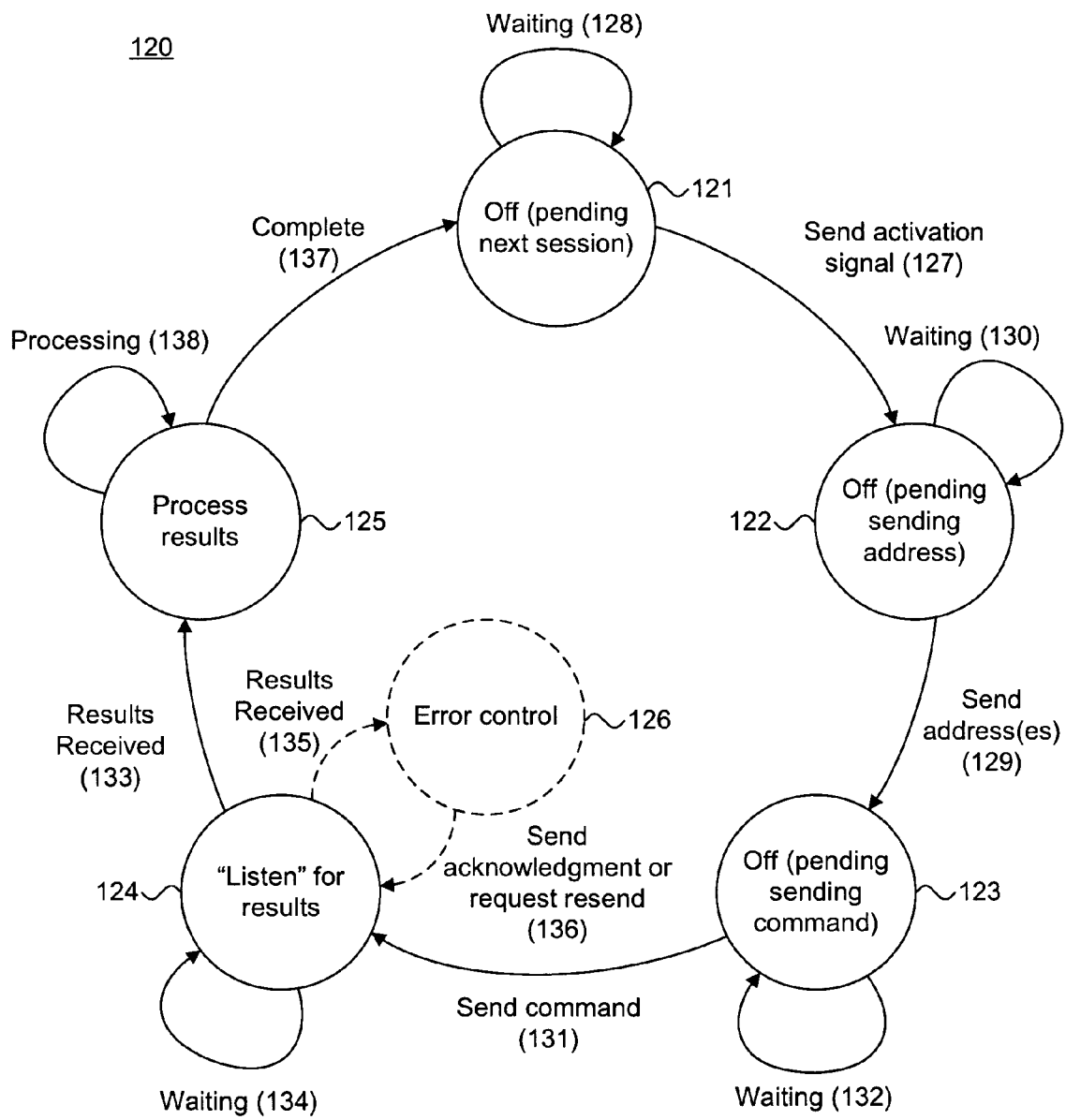
FIGS. 2A-B are state diagrams for a master-slave network configuration of the intra-body network of FIG. 1.
Figure 2B:
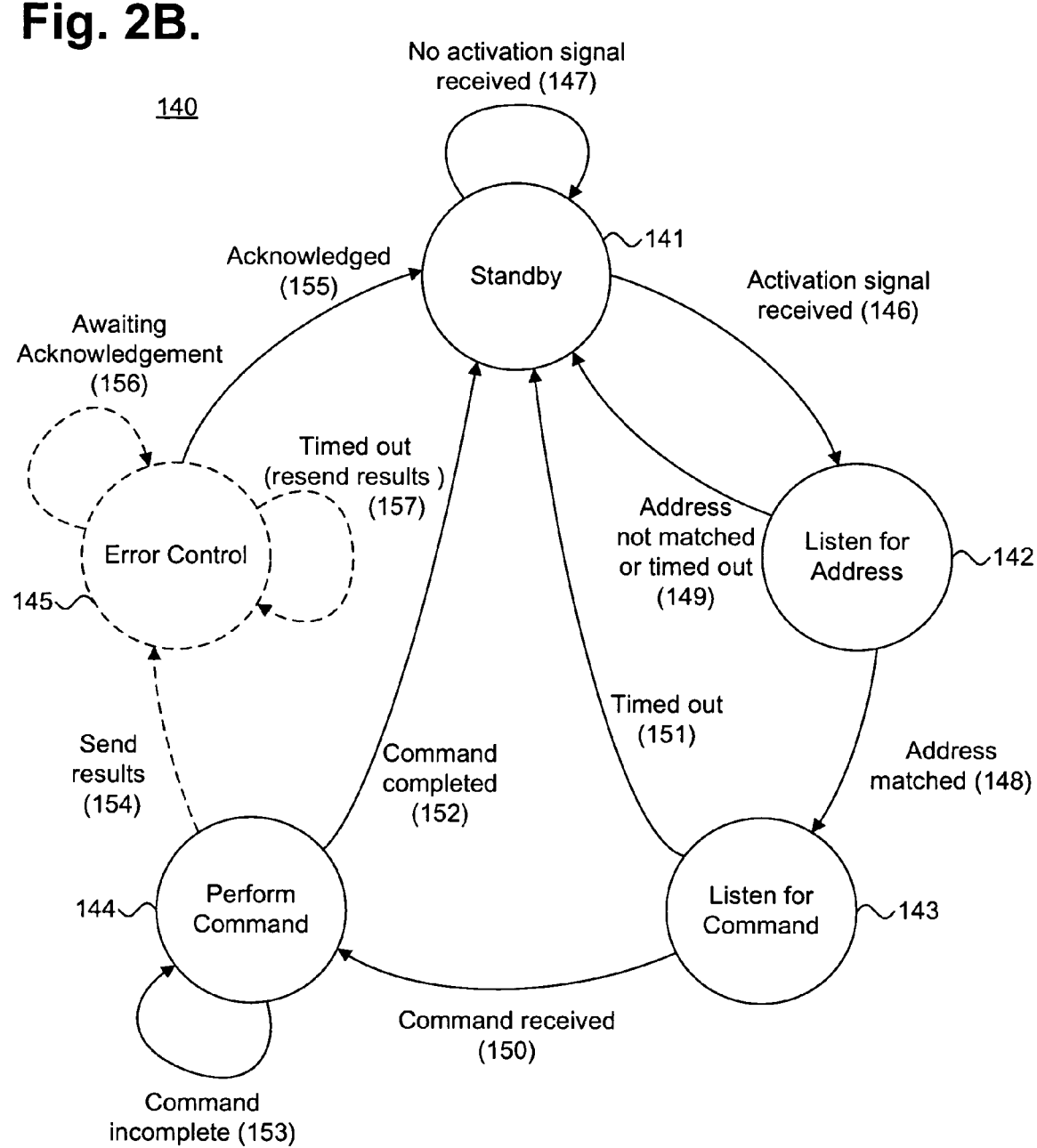

FIGS. 2A-B are state diagrams 120, 140 for a master-slave network configuration of the intra-body network 117 of FIG. 1. One or more IMDs 103 actively interface directly with at least one passive IM 116a in a master-slave network configuration. Each IMD 103 functions as a master module that initiates and controls communications with the IMs 116a serving as slave modules. Individual IMs 116a cannot initiate communications and wait in a passive standby mode until activated. In a further embodiment, however, an IM 116a can communicate with one or more other IMs 116b-d by relaying data through a common IMD 103.

Briefly, the master-slave network configuration assigns the bulk of the processing and communications burden on the IMD 103, which generally has greater processing and power capacities. Conversely, the IMs 116a-d attempt to conserve energy by responding only as requested by an IMD 103. To initiate a communications session, the master module sends a high power activation signal to awaken the slave modules from a low power standby listening mode into a high power listening mode and, following identification of one or more of the slave modules, the non-identified slave modules resume the low power standby listening mode. The use of a high power activation signal minimizes the amount of energy used by the slave modules when in a passive listening mode. The master module subsequently switches to a low power transmit mode and sends a wireless request to the identified slave modules to execute a command message. Upon completion, the slave modules send the command execution results to the master module in a wireless data packet and return to the low power standby listening mode. In a further embodiment, the slave modules remain in a high power listening mode until expressly instructed by the master module to return to the low power standby listening mode. In a still further embodiment, the IMD 103 and one or more IMs 116a perform error control to ensure error-free transmissions.

Master Module State Diagram

FIG. 2A is a state diagram 120 showing state transitions for an IMD 103 participating in a master-slave network configuration. For simplicity, authentication and arbitration between competing IMDs 103 is omitted, but is further described below with reference to FIG. 4. For purposes of master-slave network communications, each IMD 103 is either in an off state or an active state, which includes awaiting or processing command message results.

When implemented in a master-slave network configuration, the IMD 103 initiates all communications with one or more of the IMs 116a through a request push protocol, which operates in two modes. First, during a wake-up mode, the IMD 103 sends a high power activation signal to all of the IMs 116a-d in the intra-body network 117. Second, during a communicate mode, the MD 103 switches to a low power transmit mode and sends a wireless command execution request to a particular IM 116a or select set of IMs 116c-d, which perform the command message and return results back to the requesting IMD 103.

Proceeding state-by-state, the IMD 103 is initially in an Off state 121 pending the start of the next communications session. The MD 103 continues waiting (transition 128) until the communications session is initiated by the MD 103, which sends an activation signal (transition 127) to all of the IMs 116a-d in the intra-body network 117. The IMD 103 again enters an Off state 122 and continues waiting (transition 130) for a pre-determined delay while waiting for the IMs 116a to awaken from standby. In a further embodiment, rather than again entering an Off state, the IMD 103 enters an Active state. Upon expiration of the delay, the IMD 103 sends a wireless packet containing an address or range of addresses (transition 129) respectively identifying a specific IM 166a or select IMs 116c-d. The IMD 103 again enters an Off state 123 and continues waiting (transition 132) for a further pre-determined delay while waiting for the non-identified IMs 116a to resume standby. In a further embodiment, the IMD 103 similarly enters an Active state rather than again entering an Off state. Upon expiration of delay, the IMD 103 sends a wireless packet containing a command message (transition 131) to be executed by the select IM 116a or set of IMs 116c-d.

Next, the IMD 103 enters an Active state 124 to "listen" for results following command execution from the select IM 116a or set of IMs 116c-d. The IMD 103 continues waiting (transition 134) for the results for a pre-determined delay. For efficiency, the IMD 103 can "listen" by first passively waiting in an Off mode and later switching to a high sensitivity receive mode upon expiration of the delay, as results from the IMs 116a-d will only be sent to the IMD 103 upon the initiation of a communications session by the MD 103. Upon receiving the results (transition 133), the MD 103 enters an Active state 125 to process the results and continues processing (transition 138) until the processing is complete (transition 137), after which the IMD 103 again enters the Off state 121.

In a further embodiment, the IMD 103 and IMs 116a-d perform error control to ensure error-free transmissions, as further described below with reference to FIG. 11. If error control is utilized, the IMD 103 enters an error control state 126 upon receiving the results (transition 135). Depending upon outcome, the IMD 103 again enters the Active state 124 to "listen" for results following error control by either sending acknowledgement of the successful receipt of results or requesting a resending of the results (transition 136).

Slave Module State Diagram

FIG. 2B is a state diagram 140 showing state transitions for an IM 116a participating in a master-slave network configuration. For purposes of master-slave network communications, each IM 116a is either in a low power standby listening state, high power listening state or an active state, which includes executing command messages.

When implemented in a master-slave network configuration, the IM 116a passively awaits requests "pushed" by a IMD 103. The IM 116a also operates in two modes. First, during the wake-up mode, the IM 116a switches to a high power listening mode in response to a high power activation signal sent to all of the IMs 116a-d in the intra-body network 117. Second, during the communicate mode, the IM 116a listens for wireless address and, if identified, command message packets and performs the command message and returns results back to the requesting IMD 103.

Proceeding state-by-state, the IM 116a is initially in a passive Standby state 141 pending the start of the next communications session. The IM 116a remains in the Standby state 141 as long as no high power activation signal is received (transition 147) from an IMD 103. Upon receiving an activation signal (transition 146), the IM 116a enters a high power Listen state 142 to await a wireless packet containing an address or range of addresses. The IM 116a again enters the Standby state 141 if the wireless packet is received from the IMD 103, but the address or range of addresses do not match the address of the IM 116a or the IM 116a times out (transition 149). Otherwise, the IM 116a enters a high power Listen state 143 to await a wireless packet containing a command message to be executed. The IM 116a again enters the Standby state 141 if no wireless packet is received and the IM 116a times out (transition 151).

Next, upon successfully receiving the wireless packet containing a command message (transition 150), the IM 116a enters an Active state 144 to perform the command message and continues to perform the command message (transition 153). The IM 116a again enters the Standby state 141 upon command message completion with the results being sent back to the requesting IMD 103 (transition 152). In a further embodiment (not shown), the IM 116a remains in a high power listening mode by returning to Active state 144 until expressly instructed by the IMD 103 to return to the Standby state 141.

In a further embodiment, the MD 103 and IMs 116a-d perform error control to ensure error-free transmissions, as further described below with reference to FIG. 11. If error control is utilized, the IM 116a enters an error control state 145 upon sending the results (transition 154). Depending upon outcome, the IM 116a remains in the error control state 145 while awaiting acknowledgement (transition 156) from the IMD 103. Alternatively, if the IM 116a times out, the IM 116a again sends the results (transition 157) and remains in the error control state 145. The IM 116a again enters the Standby state 141 upon receipt of an acknowledgement from the IMD 103 (transition 155).

Peer-to-Peer Intra-Body Network Configuration

Figure 3A:
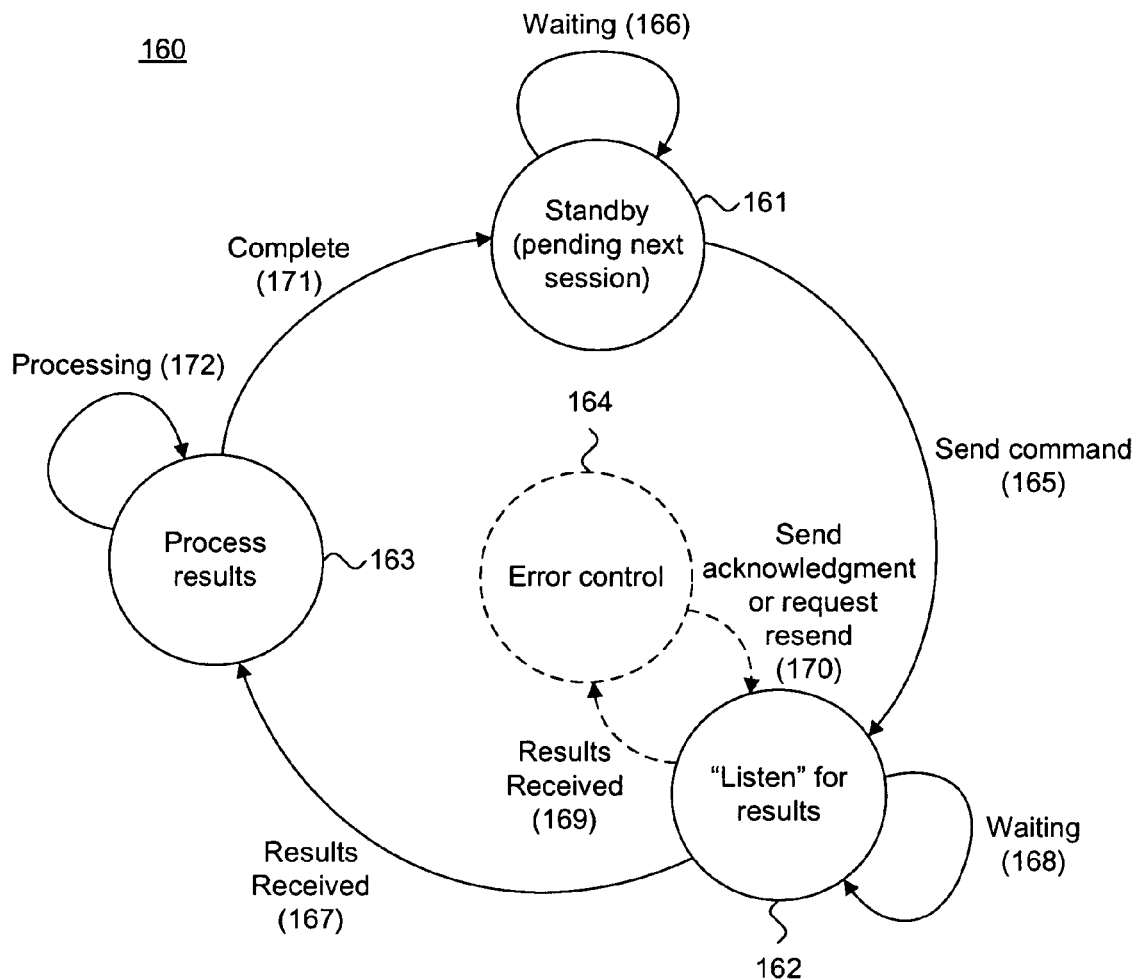
FIGS. 3A-B are state diagrams for a peer-to-peer network configuration of the intra-body network of FIG. 1.
Figure 3B:
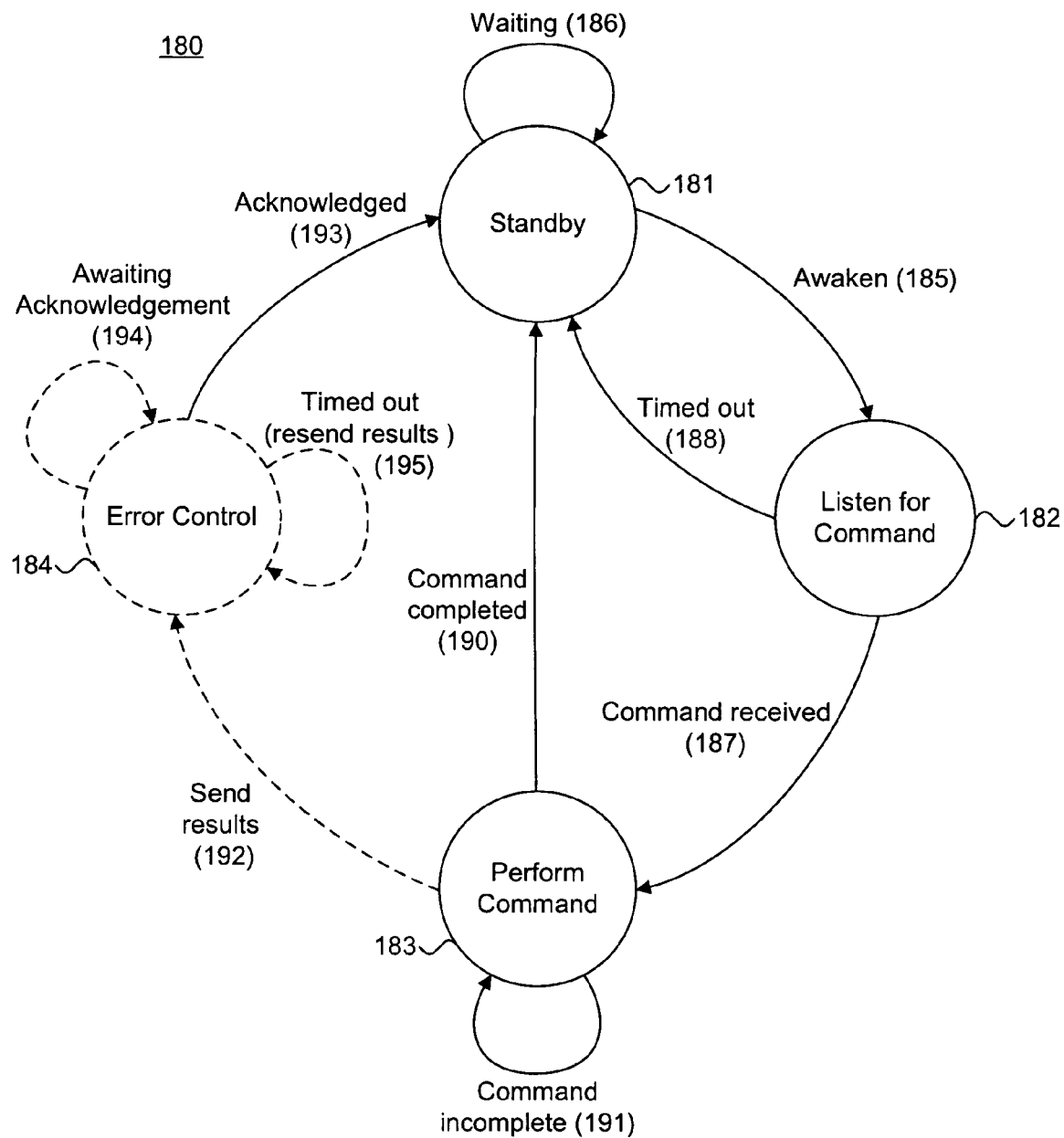

FIGS. 3A-B are state diagrams 160, 180 for a peer-to-peer network configuration of the intra-body network 117 of FIG. 1. Each IMs 116a can actively interface directly with other IMs 116b-d in a peer-to-peer network configuration with control over communications distributed amongst the individual IMs 116a. In a further embodiment, the peer-to-peer network configuration can also include one or more participating IMDs 103. Each IM 116a can function as a requesting peer that communicates directly with one or more other IMs 116b that serve as responding peers.

Briefly, the peer-to-peer network configuration enables all implantable devices, including IMDs 103 and IMs 116a-d, to communicate directly with each other. In one embodiment, communications sessions are periodically self-initiated between the cooperating IMs 116a-d, which exchange command message requests and results through wireless data packets. A requesting IM 116a and one or more responding IMs 116b-d awaken after a pre-determined delay, with the requesting IM 116a generally sending a command to the one or more responding IMs 116b-d. In a further embodiment, each IM 116a-d remains in a high power listening mode, such as during a specific event, for instance, responding to an emergency condition. In a still further embodiment, the IMs 116a-d perform error control to ensure error-free transmissions. However, the data exchanged between the requesting IM 116a and the one or more responding IMs 116b-d need not be limited to a response-request format. In a further embodiment, commands can be sent bi-directionally between the requesting IM 116a and the one or more responding IMs 116b-d. Moreover, in a still further embodiment, commands are implied and only data is exchanged between the requesting IM 116a and the one or more responding IMs 116b-d following automatic command execution.

Requesting Peer State Diagram

FIG. 3A is a state diagram 160 showing state transitions for an IM 116a functioning as a requesting peer in a peer-to-peer network configuration. For simplicity, authentication and arbitration between competing IMs 116a-d is omitted, but is further described below with reference to FIG. 5. For purposes of peer-to-peer network communications, each IM 116a is either in a low power standby listening state or an active state, which includes awaiting or processing command message results.

When implemented in a peer-to-peer network configuration, the IM 116a functioning as a requesting peer periodically initiates communications with one or more other IMs 116a functioning as responding peers through a single-mode request push protocol. Basically, the requesting IM 116a sends a wireless command execution request to a particular responding IM 116a or select group of responding IMs 116c-d, which perform the command message and return results back to the requesting IM 116a.

Proceeding state-by-state, the requesting IM 116a is initially in an Standby state 161 pending the start of the next periodic communications session. The requesting IM 116a continues waiting (transition 166) for a pre-determined delay while waiting for the scheduled start of the communications session. Upon expiration of the delay, the requesting IM 116a sends a wireless packet containing a command message (transition 165) to be executed by a pre-determined responding IM 116b or set of responding IMs 116c-d.

Next, the requesting IM 116a enters an Active state 162 to "listen" for results following command execution from the select responding IM 116b or group of responding IMs 116c-d. The requesting IM 116a continues waiting (transition 168) for the results for a pre-determined delay. For efficiency, the requesting IM 116a can "listen" by first passively waiting in a Standby mode and later switching to a high sensitivity receive mode upon expiration of the delay. Upon receiving the results (transition 167), the requesting IM 116a enters an Active state 163 to process the results and continues processing (transition 172) until the processing is complete (transition 171), after which the requesting IM 116a again enters the Standby state 161.

In a further embodiment, the requesting IM 116a and responding IMs 116b-d perform error control to ensure error-free transmissions, as further described below with reference to FIG. 11. If error control is utilized, the requesting IM 116a enters an error control state 164 upon receiving the results (transition 169). Depending upon outcome, the requesting IM 116a again enters the Active state 162 to "listen" for results following error control by either sending acknowledgement of the successful receipt of results or requesting a resending of the results (transition 170).

Responding Peer State Diagram

FIG. 3B is a state diagram 180 showing state transitions for an IM 116b functioning as a responding peer in a peer-to-peer network configuration. For purposes of peer-to-peer network communications, each IM 116b is either in a low power standby listening state, high power listening state or an active state, which includes executing command messages.

When implemented in a peer-to-peer network configuration, the responding IM 116a functions as a responding peer by periodically awakening from a standby mode to communicate with a pre-determined IMs 116a functioning as a requesting peer. Basically, the responding IM 116b receives a wireless command execution request from the requesting IM 116a, performs the command message and returns results back to the requesting IM 116a.

Proceeding state-by-state, the IM 116b is initially in a passive Standby state 181 pending the start of the next communications session. The responding IM 116b continues waiting (transition 186) for a pre-determined delay while waiting for the scheduled start of the communications session. Upon expiration of the delay, the responding IM 116b awakens (transition 185) and enters a high power Listen state 182 to await a wireless packet containing a command message to be executed. The responding IM 116b again enters the Standby state 181 if no wireless packet is received and the responding IM 116b times out (transition 188).

Next, upon successfully receiving the wireless packet containing a command message (transition 187), the responding IM 116b enters an Active state 183 to perform the command message and continues to perform the command message (transition 191). The responding IM 116b again enters the Standby state 181 upon command message completion with the results being sent back to the requesting IM 116a (transition 190).

In a further embodiment, the requesting IM 116a and responding IM 116b perform error control to ensure error-free transmissions, as further described below with reference to FIG. 11. If error control is utilized, the responding IM 116b enters an error control state 184 upon sending the results (transition 192). Depending upon outcome, the responding IM 116b remains in the error control state 184 while awaiting acknowledgement (transition 194) from the requesting IM 116a. Alternatively, if the responding IM 116b times out, the responding IM 116b again sends the results (transition 195) and remains in the error control state 184. The responding IM 116b again enters the Standby state 181 upon receipt of an acknowledgement from the requesting IM 116b (transition 193).

Master-Slave Network Configuration Timing Diagram

Figure 4:
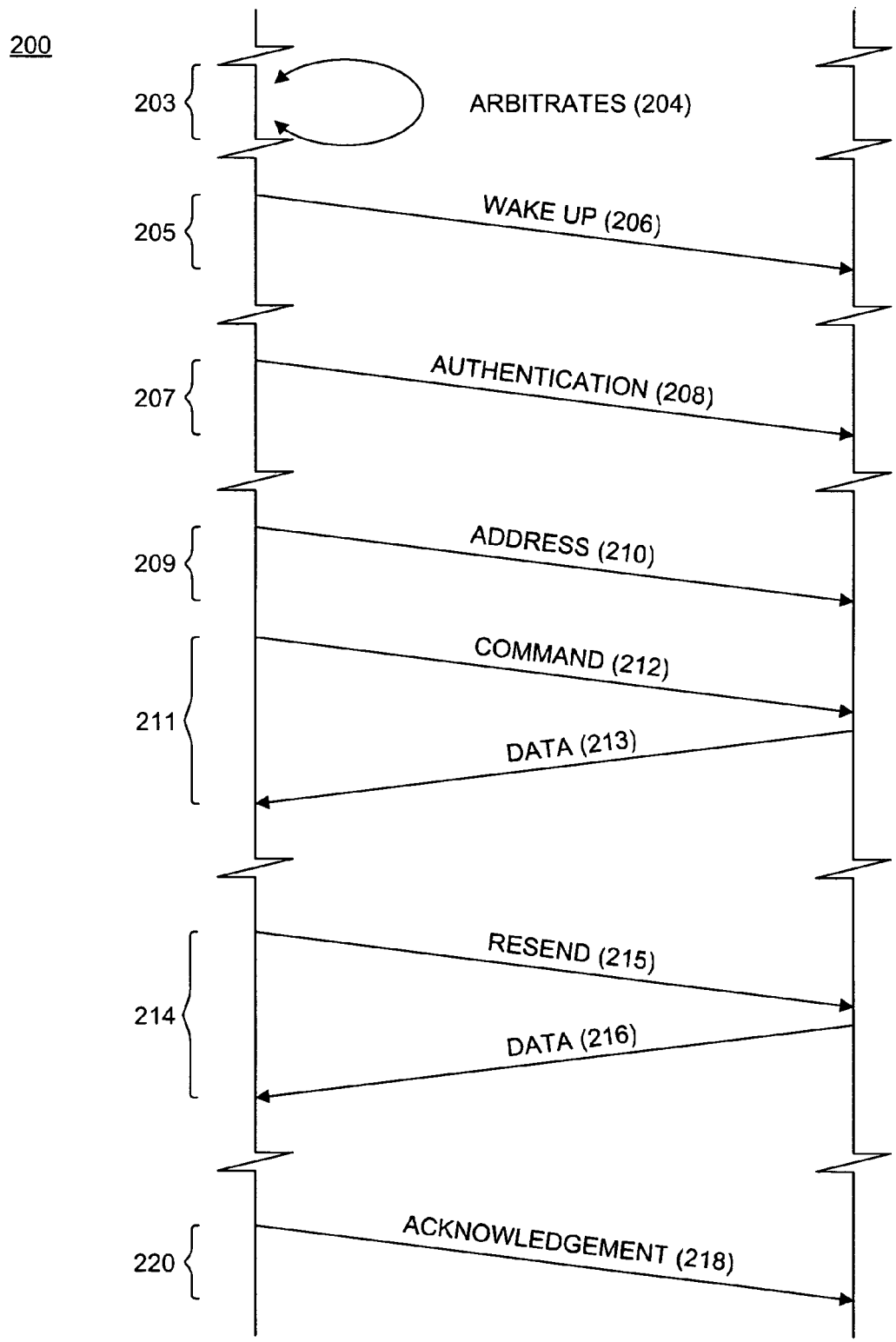
FIG. 4 is a timing diagram showing data exchange within a master-slave network configuration of the intra-body network of FIG. 1.

FIG. 4 is a timing diagram 200 showing data exchange within a master-slave network configuration of the intra-body network 117 of FIG. 1. When operating in a master-slave network configuration, communications flow in a primarily one-sided exchange, originating from an MD 103, designated as the master module 201, to one or more IMs 116a-d, each designated as a slave module 202. Generally, the only communications originating from a slave module 202 are the results generated in response to the command message received from the master module 201. Communications proceed in stages that include arbitration 203, activation 205, authentication 207, identification 209, and command execution 211. In a further embodiment, communications also include stages for performing error control that include retransmission 214 and acknowledgement 220.

Arbitration 203 is performed between competing master modules 201 to ensure that only one master module 201 is active at any given time with all other master modules 201 designated as passive listeners. During arbitration 203a would-be master module 201 first arbitrates 204 with other master modules 201 and slave modules 202 prior to sending an activation signal over the intra-body network 117 to avoid overlapping communications sessions. In one embodiment, arbitrating 204 is performed through carrier sensing, multiple access with collision avoidance (CSMA-CA). If the master module 201 detects carrier signal activity on the intra-body network 117, the master module 201 waits for a pre-determined delay before attempting to initiate a communications session. In a further embodiment, the IMD 103 and IMs 116a-d are frequency agile and a different frequency is selected if the master module 201 detects carrier signal activity on the intra-body network 117. Other forms of arbitration are possible, including carrier sensing, multiple access with collision detection (CSMA-CD) and token exchange.

Activation 205, authentication 207, identification 209 and command execution 211 constitute the primary phases of a communications session. During activation 207, the master module 201 sends a wake-up message 206, in the form of a high power activation signal, to the slave module 202, thereby causing each IM 116*a* to transition to a high power receiving state.

Authentication 207 provides security and dynamic resource discovery of slave modules 202 participating on the intra-body network 117. During authentication 207, the master module 201 sends an authentication message 206 to each potential slave module 202 and communications sessions are performed following successful authentication. In a further embodiment, authentication 207 is implicit and each master module 201 is statically programmed with the addresses of slave modules 202 with which the master module 201 can communicate. In a still further embodiment, the set of known, the credentials of authenticated slave modules 202 can be transferred to a new master module 201, rather than requiring the new master module 201 and slave modules 202 to repeat the authentication process, which can be computationally time-consuming and resource intensive, particularly, relative to power usage.

Authentication 207 is typically only performed once when a new master module 201 or new slave module 202 joins the intra-body network 117. In one embodiment, the authentication 173 can be provided through a secret key shared by the master module 201 and slave module 202. In a further embodiment, a public-private key pairing is used. In a still further embodiment, a secret key with a unique network address is assigned to a specific slave module 202. Other forms of authentication are possible. In addition, in a further embodiment, authentication 207 is performed during each communications session.

During identification 209, the master module 201 switches to a low power transmit mode and sends an address message 210 identifying either a specific IM 116*a* or a set of IMs 116*c-d*, each as a slave module 202. During command execution 211, the master module 201 sends a command message 212 requesting the execution of a command message by the slave module 202, which is acknowledged by the sending back of a data message 213 containing the results of the command execution. Generally, the command message 212 instructs the specific IM 166*a* or set of IMs 116*c-d* to perform an autonomous therapeutic or sensing function or other such function as performable by the specific IM 166*a* or set of IMs 116*c-d*. In a further embodiment, an IM 116*a* can communicate with one or more other IMs 116*b-d* by relaying data through a common IMD 103 in the form of a command message 212.

In a further embodiment, retransmission 214 and acknowledgement 220 are performed to provide error control. During retransmission 214, the master module 201 sends a resend message 215 to the slave module 202 in the event of an error in the original data packet 213. The master module 201 then receives back a retransmitted data message 216. Finally, during acknowledgement 220, the master module 201 sends an acknowledgement message 218 to signify the successful receipt of the data packet 213.

Peer-to-Peer Network Configuration Timing Diagram

Figure 5:
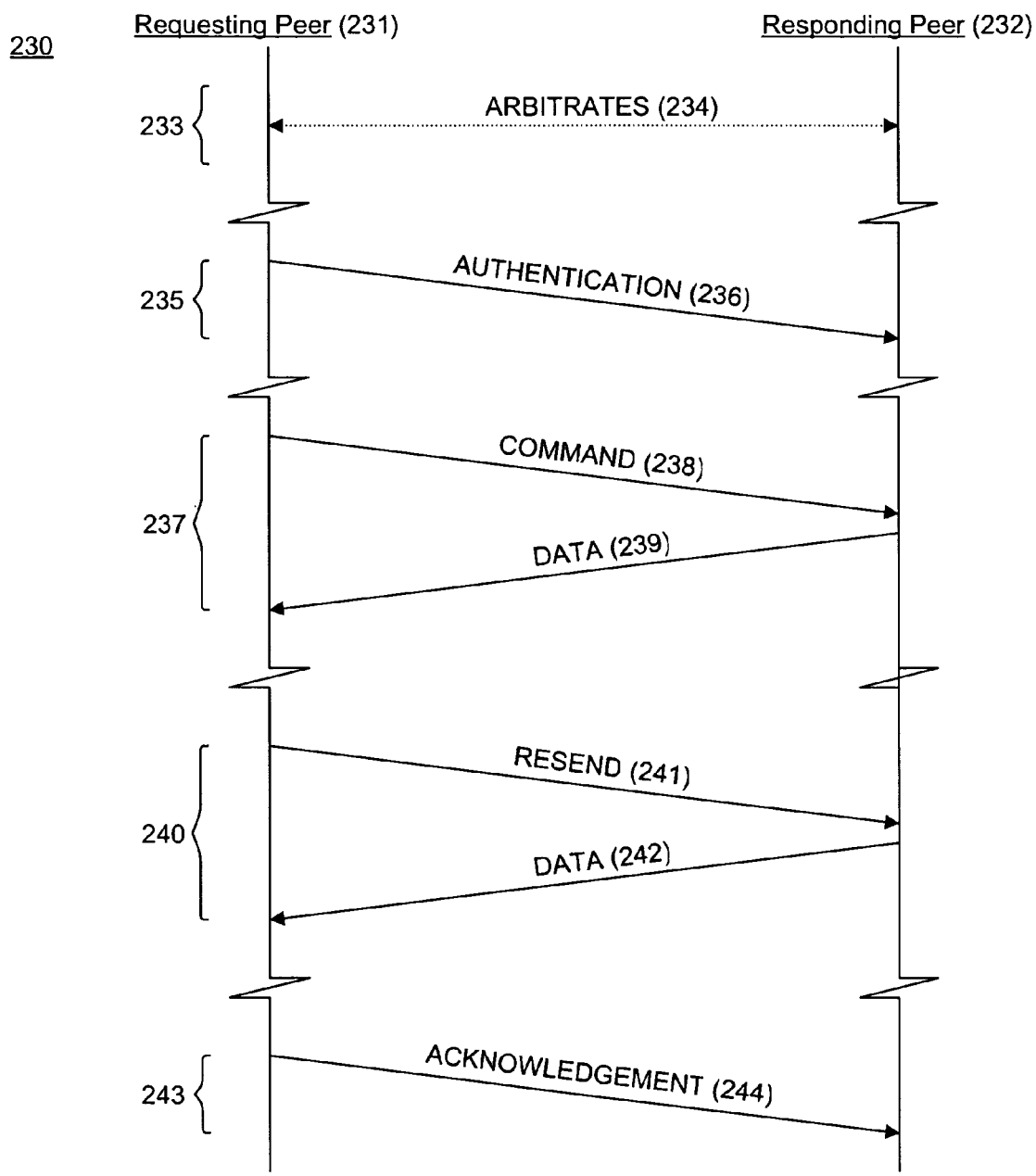
FIG. 5 is a timing diagram showing data exchange within a peer-to-peer network configuration of the intra-body network of FIG. 1.

FIG. 5 is a timing diagram 230 showing data exchange within a peer-to-peer network configuration of the intra-body network 117 of FIG. 1. When operating in a peer-to-peer network configuration, communications flow back and forth between the one IM 116*a*, designated as a requesting peer 231, and the one or more IMs 116*b-d*, each designated as a responding peer 232. Communications proceed in stages that include arbitration 233, authentication 235 and command execution 237. In a further embodiment, communications also include stages for performing error control that include retransmission 240 and acknowledgement 243.

Arbitration 233 is performed between competing requesting peers 231 to ensure that only one requesting peer 231 is active at any given time with all other requesting peers 231 remaining in standby mode. During arbitration 233, a would-be requesting peer 231 first arbitrates 234 with other requesting peers 231 and responding peers 232 prior to sending a command message request over the intra-body network 117 to avoid overlapping communications sessions. In one embodiment, arbitration 233 is performed implicitly by assigning different pre-determined delays to each requesting peer 231. In a further embodiment, arbitrating 234 is performed through carrier sensing, multiple access with collision avoidance (CSMA-CA). If the requesting peer 231 detects carrier signal activity on the intra-body network 117, the requesting peer 231 waits for a pre-determined delay before attempting to initiate a communications session. In a still further embodiment, the IMs 116*a-d* are frequency agile and a different frequency is selected if the requesting peer 231 detects carrier signal activity on the intra-body network 117. Other forms of arbitration are possible, including carrier sensing, multiple access with collision detection (CSMA-CD) and token exchange.

Authentication 235 and command execution 237 constitute the primary phases of a communications session. Authentication 235 provides security and dynamic resource discovery of responding peers 232 participating on the intra-body network 117. During authentication 235, the requesting peer 231 sends an authentication message 236 to each potential responding peer 232 and communications sessions are performed following successful authentication. In a further embodiment, authentication 235 is implicit and each requesting peer 231 is statically programmed with the addresses of responding peers 232 with which the requesting peer 231 can communicate.

Authentication 235 is typically only performed once when a new requesting peer 231 or responding peer 232 joins the intra-body network 117. In one embodiment, the authentication 235 can be provided through a secret key shared by the requesting peer 231 and responding peer 232. In a further embodiment, a public-private key pairing is used. In a still further embodiment, a secret key with a unique network address is assigned to a specific responding peer 232. Other forms of authentication are possible. During command execution 211, the requesting peer 231 sends a command message 238 requesting the execution of a command message by the responding peer 232, which is acknowledged by the sending back of a data message 239 containing the results of the command execution.

In a further embodiment, retransmission 240 and acknowledgement 243 are performed to provide error control. During retransmission 240, the requesting peer 231 sends a resend message 241 to the responding peer 232 in the event of an error in the original data packet 239. The requesting peer 231 then receives back a retransmitted data message 242. Finally, during acknowledgement 243, the requesting peer 231 sends an acknowledgement message 244 to signify the successful receipt of the data packet 239.

External Interfaces

The IMDs 103 and IMs 116a-d can communicate autonomously through digital data exchange within the intra-body network 117 when structured in either a master-slave or peer-to-peer network configuration. In addition, the IMDs 103 and IMs 116a-d can be interfaced to an external device, such as a programmer, repeater or similar device, to perform programming, troubleshooting, recharging and to exchange parametric and physiological data. In a further embodiment, one or more external devices can function as a master module 201 to interface directly with at least one IMD 103 or IM 116a functioning as slave modules 202. For simplicity, authentication and arbitration between each external device and competing IMDs 103 and IMs 116a is omitted, but is performed in a manner analogous to authentication and arbitration in a master-slave network configuration, as further described above with reference to FIG. 4.

Programmer-Based External Interface

FIG. 6 is a functional block diagram 250 showing, by way of example, a programmer-based external interface with a wireless intra-body network 117. For short-range data exchange, the IMD 103 communicates with a programmer 251 through induction or similar forms of near-field telemetry. Inductive signals are exchanged through a wand 252 placed over the location of the IMD 103. Programming or interrogating instructions are sent to the IMD 103 and stored physiological data is downloaded into the programmer 251. For long range data exchange, the IMD 103 communicates with a programmer 251 through radio frequency (RF) or other forms of far-field telemetry. In a further embodiment, the IMs 116a-d also communicate with the programmer 251. In addition, other types short and long range data exchange interfaces are possible.

In a further embodiment, the downloaded physiological data is sent via a network 253, such as the Internet, to a data server 254, which maintains a database 255. The data server 254 stores the physiological data in the database 255 in patient records 256. In addition, the stored physiological data can be evaluated and matched as quantitative pathophysiological measures against one or more medical conditions, such as described in related, commonly-owned U.S. Pat. No. 6,336,903, to Bardy, issued Jan. 8, 2002; U.S. Pat. No. 6,368,284, to Bardy, issued Apr. 9, 2002; U.S. Pat. No. 6,398,728, to Bardy, issued Jun. 2, 2002; U.S. Pat. No. 6,411,840, to Bardy, issued Jun. 25, 2002; and U.S. Pat. No. 6,440,066, to Bardy, issued Aug. 27, 2002, the disclosures of which are incorporated by reference.

An example of a programmer with inductive telemetry is the Model 2920 Programmer Recorder Monitor, manufactured by Guidant Corporation, Indianapolis, Ind., which includes the capability to store retrieved raw physiological signals on a removable floppy diskette. The raw physiological signals can later be electronically transferred using a personal computer or similar processing device.

Repeater-Based External Interface

FIG. 7 is a functional block diagram 260 showing, by way of example, a repeater-based external interface with a wireless intra-body network 117. For short-range data exchange, the IMD 103 communicates with a repeater 261 through induction or similar forms of near-field telemetry. Unlike a programmer 251, the repeater 261 is assigned to a single IMD 103 for a particular patient's exclusive use and allows data upload and reprogramming settings download on an IMD-specific basis only upon successful registration. Inductive signals are exchanged through a wand 262 placed over the location of the IMD 103. Programming or interrogating instructions are sent to the IMD 103 and stored physiological data is downloaded into the programmer 261. For long range data exchange, the IMD 103 communicates with a repeater 261 through radio frequency (RF) or other forms of far-field telemetry. In a further embodiment, the IMs 116a-d also communicate with the repeater 261. In addition, other types short and long range data exchange interfaces are possible.

In a further embodiment, the downloaded physiological data is sent via a network 253, such as the Internet, to a data server 254, which maintains a database 255. The data server 254 stores the physiological data in the database 255 in patient records 256. In addition, the stored physiological data can be evaluated and matched as quantitative pathophysiological measures against one or more medical conditions, such as described in related, commonly-owned U.S. Pat. No. 6,336,903, to Bardy, issued Jan. 8, 2002; U.S. Pat. No. 6,368,284, to Bardy, issued Apr. 9, 2002; U.S. Pat. No. 6,398,728, to Bardy, issued Jun. 2, 2002; U.S. Pat. No. 6,411,840, to Bardy, issued Jun. 25, 2002; and U.S. Pat. No. 6,440,066, to Bardy, issued Aug. 27, 2002, the disclosures of which are incorporated by reference.

Recharger-Based External Interface

Figure 8:
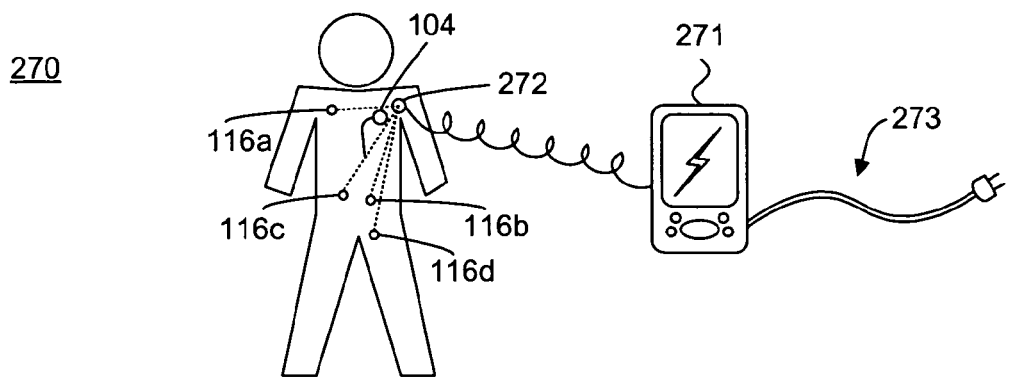
FIG. 8 is a functional block diagram showing, by way of example, a recharger-based external interface with a wireless intra-body network.

FIG. 8 is a functional block diagram 210 showing, by way of example, a recharger-based external interface with a wireless intra-body network 117. The recharger 271 is connected to a power supply 273 and provides recharging to implantable devices, such as an IMD 103 or IMs 116a-d, through induction or similar forms of indirect charging. Inductive signals are exchanged through a wand 272 placed over the location of the IMD 103 or IMs 116a-d to recharge the internal power supply of the implantable device.

Implantable Module Functional Components

Figure 9:
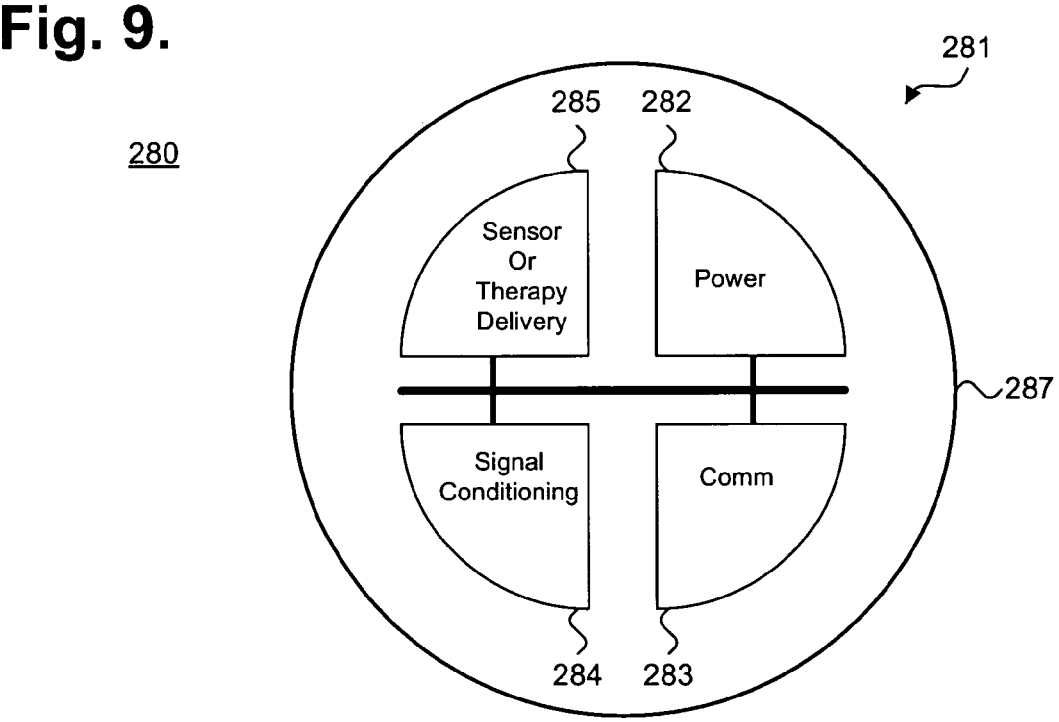
FIG. 9 is a block diagram showing the functional components implemented by an implantable module.

FIG. 9 is a block diagram 280 showing the functional components implemented by an implantable module 281. Each implantable module 281 includes solid state electronic components for providing power 282, communications 283, signal conditioning 284, and sensor or therapy delivery 285. The components are interconnected within a hermetically sealed housing 287, preferably constructed from a functionally inert protective material, such as titanium, silicone or epoxy. In one embodiment, the housing 287 is smaller than one $cm^2$ in size. Other sizes and types of housings and materials are possible.

The power component 282 is preferably a primary battery, rechargeable battery or capacitive power source, with a minimum power capacity of a few hundred micro-amp hours, although higher capacity power components could also be used. The communications component 283 provides an external interface through which the IM 281 communicates with IMDs in a master-slave network configuration, with other IMs in peer-to-peer network configuration and with external devices, such as a programmer, repeater or recharger. In one embodiment, the communication component 283 is configured to communicate through an acoustic signal, although optical, electronic field, inductive, RF or a combined interface could also be used. The communication component 283 transmits by exciting piezoelectric material at a pre-defined frequency, as further described below with reference to FIG. 10. The signal-conditioning component 284 converts results generated by the sensor or therapy delivery component 285 into digitized form suitable for packetizing prior to transmission over the communication component 283. Finally, the sensor or therapy delivery component 285 respectively monitors physiological data or delivers therapy to the patient. Physiological data non-exclusively includes pressure, temperature, impedance, strain, fluid flow, chemistry, electrical properties, magnetic properties, PH, and concentration.

Therapy non-exclusively includes cardiac resynchronization, defibrillation, neural stimulation and drug delivery. Other selections, arrangements and configurations of components are possible.

Network Protocol Stack

Figure 10:
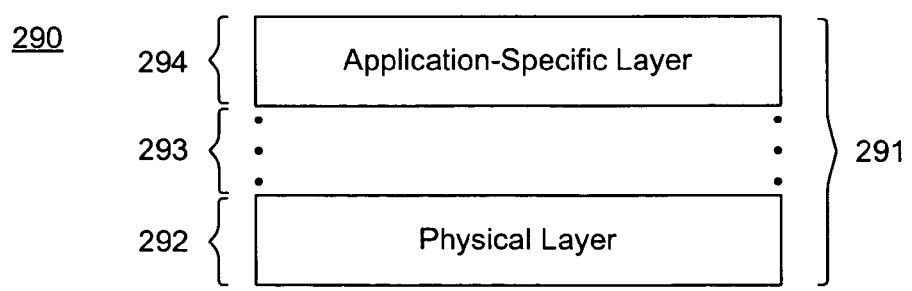
FIG. 10 is a block diagram showing a network protocol stack implemented within the intra-body network.

FIG. 10 is a block diagram 290 showing a network protocol stack 291 implemented within the intra-body network 117. A network protocol stack 291 is logically defined by each IMD 103, IM 116a-d and, in a further embodiment, external device. The network protocol stack 291 is used to implement a network communications protocol for exchanging command messages and results during a communications session. The network protocol stack 291 includes hierarchically organized protocol layers that include a lower-level physical layer 292 and can include one or more application-specific layers 294. In a further embodiment, the network protocol stack 291 can also include one or more intermediate layers 293, such as data link, network and transport layers between the physical layer 292 and the application-specific layers 294.

The physical layer 292 specifies the physical interfacing conventions, including the carrier and signal modulation, used by the IMDs 103 and IMs 116a-d participating in the intra-body network 117. In one embodiment, signals are exchanged between the IMDs 103 and IMs 116a-d with a 35 to 45 kHz acoustic carrier, which is modulated through On Off Keying (OOK). The frequency of this acoustic carrier is too high to be audible by a patient, but has a wavelength long enough to penetrate the housings of the IMDs 103 and IMs 116a-d, as well as bone and other internal body structures. OOK offers high signal efficiency expends energy only for '1' bits and no energy for '0' bits. Alternatively, ASK, FSK or PSK signal modulation could be used, as well as other types of carriers, including optical, electronic field, inductive, RF or combined carriers. Finally, as is conventional in wireless communications, carrier signals are preceded by preamble and synchronization bits, which allow wireless reception at each implantable device to settle prior to transmission of data bits.

In the one embodiment, the piezoelectric material can be excited at different levels to save energy. In a master-slave network configuration, an IMD 103 functioning as a master module 201 sends an activation signal by exciting piezoelectric material at 12 volts to generate an acoustic signal in the 35 to 45 kHz frequency range, but subsequently switches to exciting the piezoelectric material at 1 volt, as the IMs 116a-d would have then switched to high power receive modes. In a peer-to-peer network configuration, requesting IM 116a and responding IMs 116b switch to high power receive modes based on a timer, so the piezoelectric material need only be excited at 1 volt.

In general, the intermediate layers 292 and application-specific layers 294 specify packet structure and routing, and, in a further embodiment, error control. The application-specific layers 294 handle details for particular applications used by the IMDs 103 and IMs 116a-d participating in the intra-body network 117. In one embodiment, a physical layer 292 and an application-specific layer 294 can be specified as a lightweight network protocol.

The intermediate layers 292 and application-specific layers 294 rely on the physical layer 292 to ensure bitwise data transmission between communicating devices. Digital data is physically exchanged in the physical layer 292 between implantable devices in data frames, which encapsulate data packets assembled by the intermediate layers 292 and application-specific layers 294. Thus, for outbound data, the intermediate layers 292 and application-specific layers 294 are responsible for assembling data into data packets, which can be recursively encapsulated by each protocol layer. In turn, the physical layer 292 is responsible for modulating the data packet in a data frame over a carrier signal. For inbound data, the physical layer 292 is responsible for demodulating the carrier signal from a bit stream back into a data frame, which is provided as a data packet for disassembly by the intermediate layers 292 and application-specific layers 294. In a further embodiment, the data framing is performed by a data link layer executing above the physical layer 292 and implementing a point-to-point data exchange protocol, such as the various forms of IEEE 802.11, also known as Wireless Fidelity (WiFi) or Bluetooth. Other point-to-point data exchange protocols are possible.

Data Frame Data Structure

Figure 11:
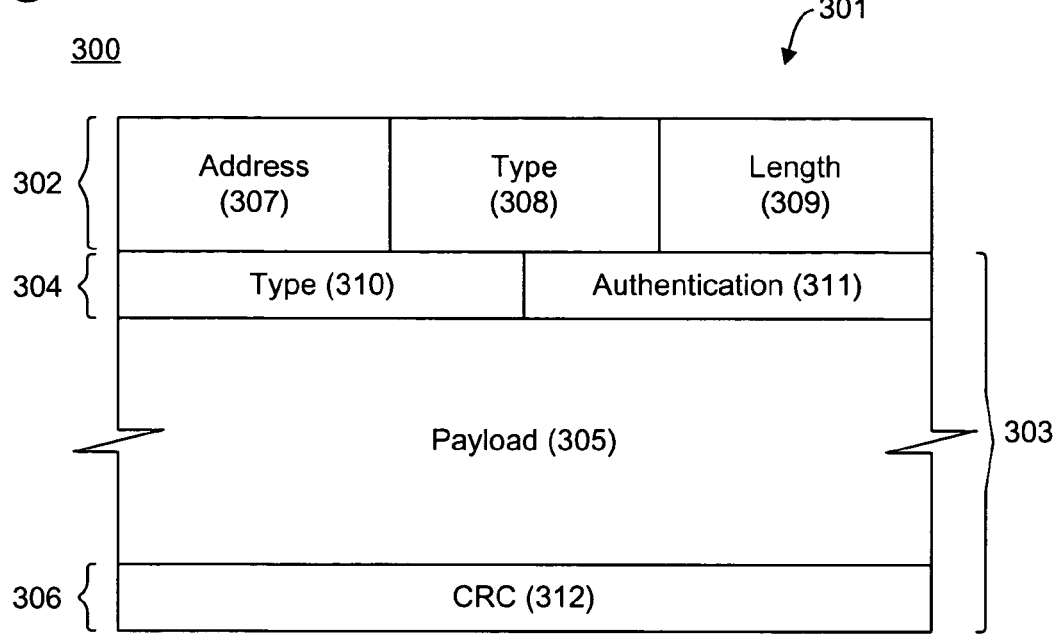
FIG. 11 is a data structure diagram showing a data frame for exchanging data within the intra-body network.

FIG. 11 is a data structure diagram showing a data frame 301 for exchanging data within the intra-body network 117. Data frames 301 are exchanged between physical protocol layers 292 and encapsulate data packets 303 assembled by the intermediate layers 292 and application-specific layers 293.

Each data frame 301 includes a data frame header 302 supporting data packet routing. The data frame header 302 includes address 307, type 308 and length 309 fields. The address field 307 identifies the destination implantable device, whether an IMD 103, IM 116a or, in a further embodiment, an external device. In one embodiment, the address field 307 supports a four-bit address space. In a further embodiment, the address field 307 supports an eight-bit address space with four-bits reserved for specifying a set of IMDs 116a-d. The type field 308 identifies a message type, such as indicating whether the data frame contains a broadcast message, should be processed only by the IM 116a with a matching address and so forth. The length field 309 specifies the length of the data packet 303, which can be used to arbitrate communications sessions. Other data frame structures and arrangements are possible.

The format of the data packet 303 depends on the intermediate layers 292 and application-specific layers 293, but typically includes a data packet header 304, payload 305 and an optional trailer 312. By way of example, the data packet header 304 can include type 310 and authentication 311 fields. The type field 310 indicates the type of data being sent as the payload 305. The authentication field 311 is used by newly-introduced implantable devices and, in a further embodiment, external devices, to mutually authenticate credentials prior to initiating a communications session. The authentication field 311 can communicate, by way of example, a shared secret key, public-private key pairing or secret key in combination with a unique network address. Other data packet structures and arrangements are possible.

In a further embodiment, error control is used by the implantable devices and, in a further embodiment, external devices to ensure error free data transmission in the intermediate layers 292 and application-specific layers 293. In one embodiment, each data packet 303 includes a trailer 306 that contains an eight-bit cyclic redundancy code (CRC) 312. Data packets are resent only upon the detection of an error by the receiving device upon calculation of the CRC 312. In a further embodiment, the CRC 312 is omitted and data is sent without specific error detection. Lower-level errors are tolerated by the receiving device and extraneous data packets are discarded as necessary. In a still further embodiment, parity bits are added in lieu of the CRC 312. Finally, in a still further embodiment, a stateless form of error control is employed. A responding device sends a data packet and, if an error is detected, the requesting device reawakens the responding device and repeats the earlier-sent command message. Consequently, the responding device need not maintain a copy of the data packet sent pending acknowledgement by the receiving device. Other forms of error control are possible.

Master Module Method Overview

Figure 12:
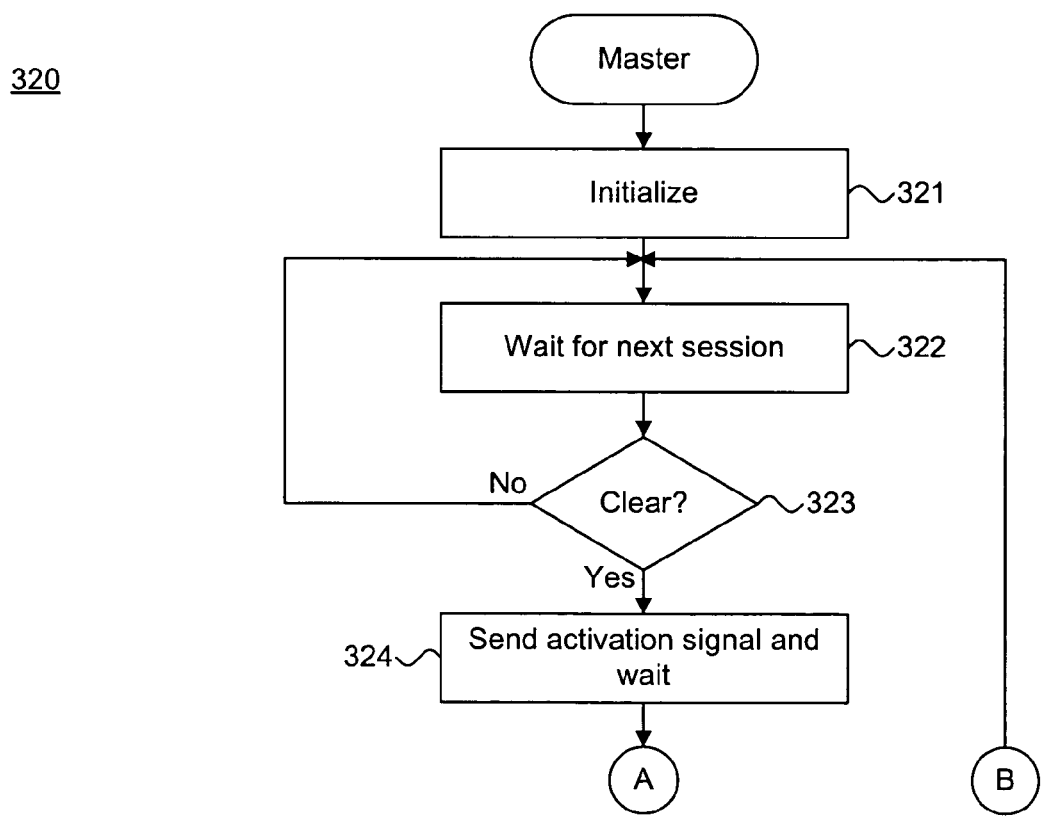
FIG. 12 is a flow diagram showing a method for providing digital data communications over a wireless intra-body network from a master module, in accordance with an embodiment of the invention.
Figure 12:
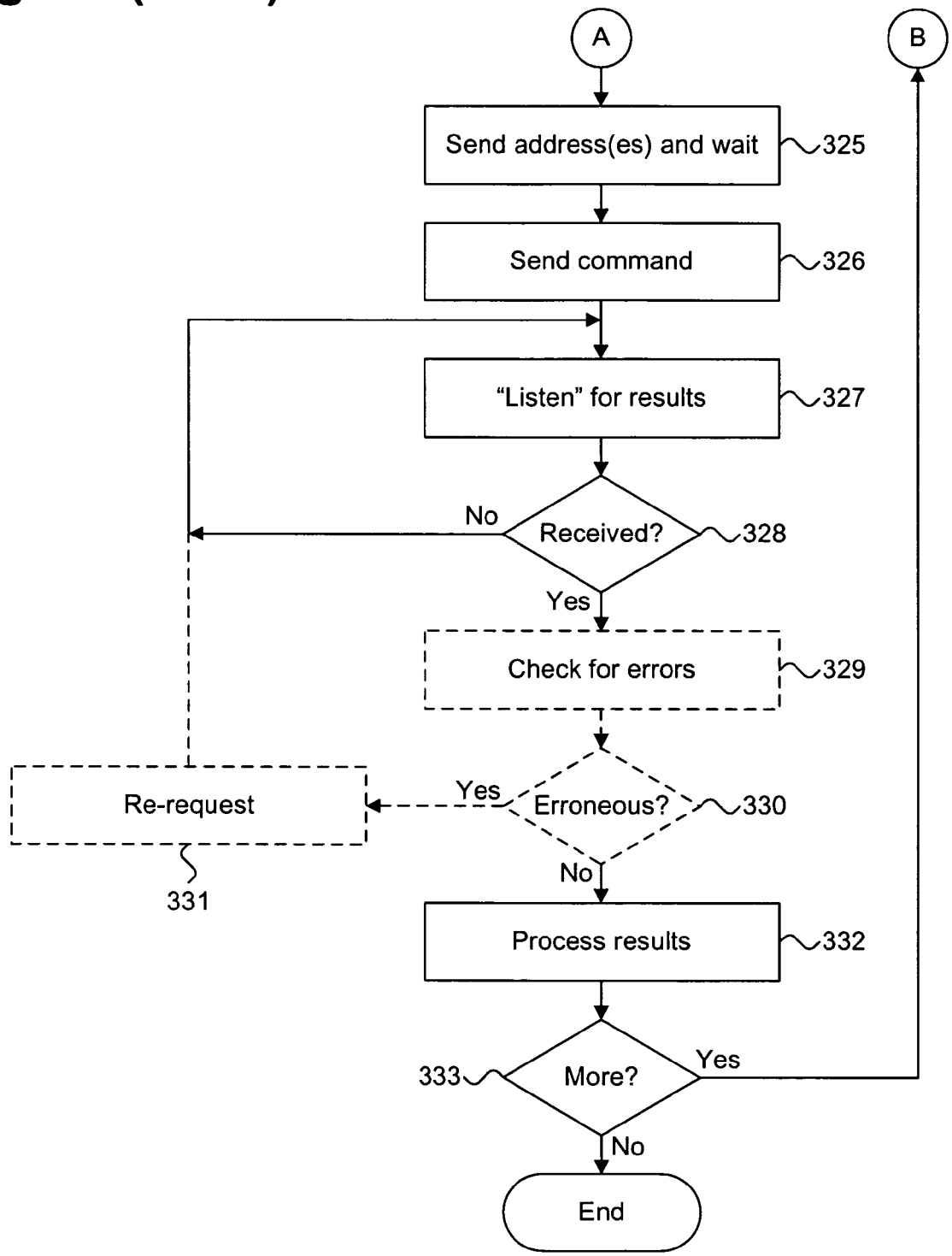

FIG. 12 is a flow diagram showing a method 320 for providing digital data communications over a wireless intra-body network 117 from a master module 201, in accordance with an embodiment of the invention. The master-slave network configuration assigns the bulk of the processing and communications burden on the IMD 103, which generally has greater processing and power capacities. The method 320 is described as a sequence of process operations or steps, which can be executed, for instance, by an IMD 103 in a master-slave network configuration.

Each master module 201 begins by initializing (block 321), which can include performing authentication 203 (shown in FIG. 4). The master module 201 is then ready to begin communications with one or more slave modules 202 (blocks 322-333). The master module 201 initiates each communications session, while each specific slave module 202 or set of slave modules 202 passively wait in a standby mode. A communications session can be started by the master module 201 at pre-determined times or as necessary. After waiting to begin the next communications session (block 322), the master module 201 performs arbitration 205 by checking for a clear communications channel (block 323). If the communications channel is not clear (block 323), the master module 201 continues waiting (block 322). Otherwise, the master module 201 sends a high power activation signal and waits for a predetermined delay (block 324). The master module 201 then switches to a low power transmit mode and sends one or more addresses respectively to a specific IM 116a or set of IMs 116c-d and waits for a further delay (block 325).

Next, the master module 201 sends a command message (block 326) and "listens" for results (block 327) to be received back from the specific IM 166a or set of IMs 116c-d. Generally, the command message instructs the specific IM 166a or set of IMs 116c-d to perform an autonomous therapeutic or sensing function or other such function as performable by the specific IM 166a or set of IMs 116c-d. In a further embodiment, an IM 116a can communicate with one or more other IMs 116b-d by relaying data through a common IMD 103 in the form of a command message. If the results have not yet been received (block 328), the master module 201 continues "listening" for results (block 327). Otherwise, in a further embodiment, the master module 201 checks the results for errors (block 329). If errors are detected (block 330), the master module 201 re-requests that the results be resent (block 332). Otherwise, the master module 201 processes the results (block 332) and, if more communications sessions are required (block 333), the master module 201 continues to wait for the next communications session (block 322). Otherwise, the method terminates.

Slave Module Method Overview

Figure 13:
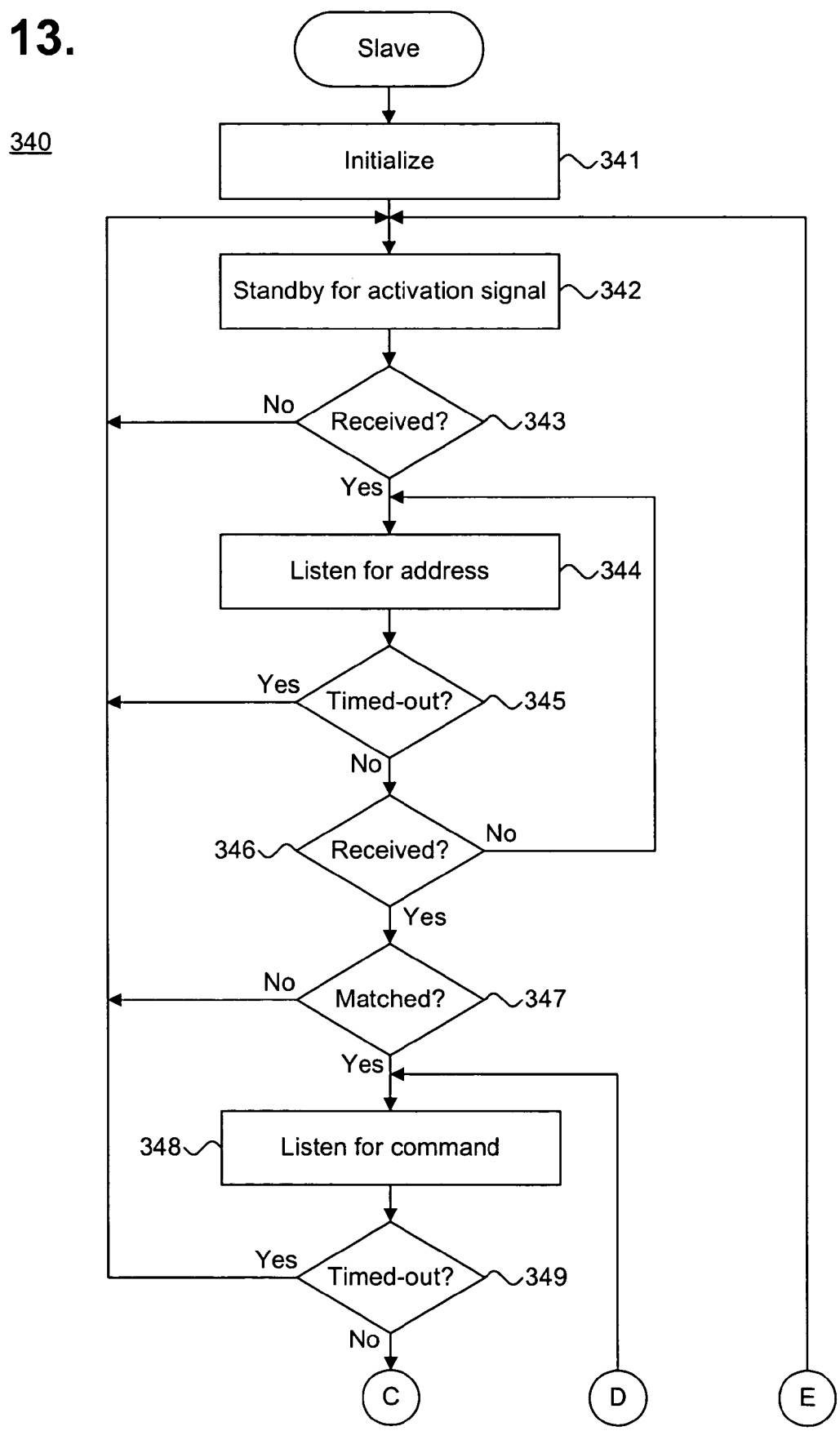
FIG. 13 is a flow diagram showing a method for providing digital data communications over a wireless intra-body network from a slave module, in accordance with an embodiment of the invention.
Figure 13:
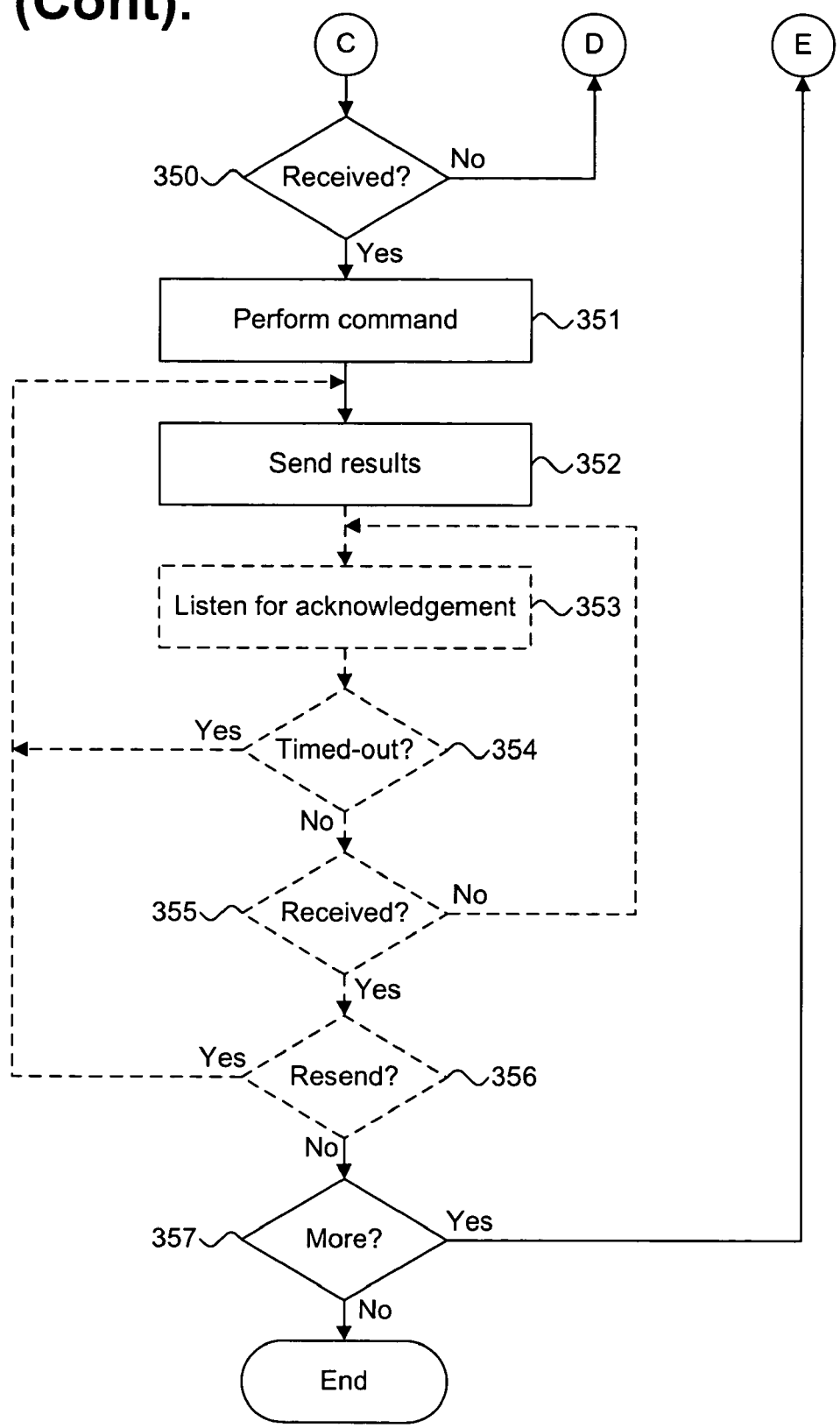

FIG. 13 is a flow diagram showing a method 340 for providing digital data communications over a wireless intra-body network 117 from a slave module 202, in accordance with an embodiment of the invention. In the master-slave network configuration, the IMs 116a-d attempt to conserve energy by responding only as requested by an IMD 103. The method 340 is described as a sequence of process operations or steps, which can be executed, for instance, by an IM 116a in a master-slave network configuration.

Each slave module 202 begins by initializing (block 341), which can include performing authentication 203 (shown in FIG. 4). The slave module 202 is then ready to begin communications with one or more master modules 201 (blocks 342-357). Each IM 116a operates in a respond-only mode and remains in a low power receive standby mode awaiting an activation signal from a master module 201 (block 342). The slave module 202 remains in the standby mode as long as an activation signal has not been received (block 343). However, once an activation signal has been received (block 343), the slave module 202 switches to a high power receive mode and "listens" for an address packet sent from the requesting master module 201 (block 335). If, after a predetermined delay, no address packet has been received, the slave module 202 times out (block 345) and returns to the standby mode (block 342). Otherwise, if an address packet has not yet been received (block 346) and the slave module 202 has not yet timed out (block 345), the slave module 202 continues "listening" for an address packet (block 335).

If an address packet has been received (block 346), but the address or range of addresses specified in the address packet does not match the address of the slave module 202 (block 347), the slave module 202 returns to the standby mode (block 342). Otherwise, if the address or range of addresses match (block 347), the slave module 202 "listens" for a command message packet sent from the requesting master module 201 (block 348). If, after a predetermined delay, no command message packet has been received, the slave module 202 times out (block 349) and returns to the standby mode (block 342). Otherwise, if the command message has not yet been received (block 350) and the slave module 202 has not yet timed out (block 349), the slave module 202 continues to "listen" for a command message packet (block 348).

If a command message packet has been received (block 350), the command message is performed (block 351), which, in one embodiment, can include performing one or more actions, such as monitoring or delivering therapy. Upon completion of the command message, the results of the command message are sent to the requesting master module 201 (block 352). Otherwise, in a further embodiment, the slave module 202 "listens" for an acknowledgement while the master module 201 checks the results for errors (block 353). If, after a predetermined delay, no acknowledgement packet has been received, the slave module 202 times out (block 354) and resends the results (block 352). Otherwise, if an acknowledgement packet has not yet been received (block 355) and the slave module 202 has not yet timed out (block 354), the slave module 202 continues "listening" for an acknowledgement packet (block 353). If errors are detected, the master module 201 will re-requests that the results be resent (block 356). Otherwise, upon receiving an acknowledgement packet (block 355), if no request to resend the results has been sent by the master module 201 (block 356), and, if more communications sessions are required (block 357), the slave module 202 returns to the standby mode (block 342). Otherwise, the method terminates. In a further embodiment (not shown), the slave module 202 remains in a high power listening mode to "listen" for a command message packet (block 348) until expressly instructed by the master module to return to the standby mode.

Requesting Peer Method Overview

Figure 14:
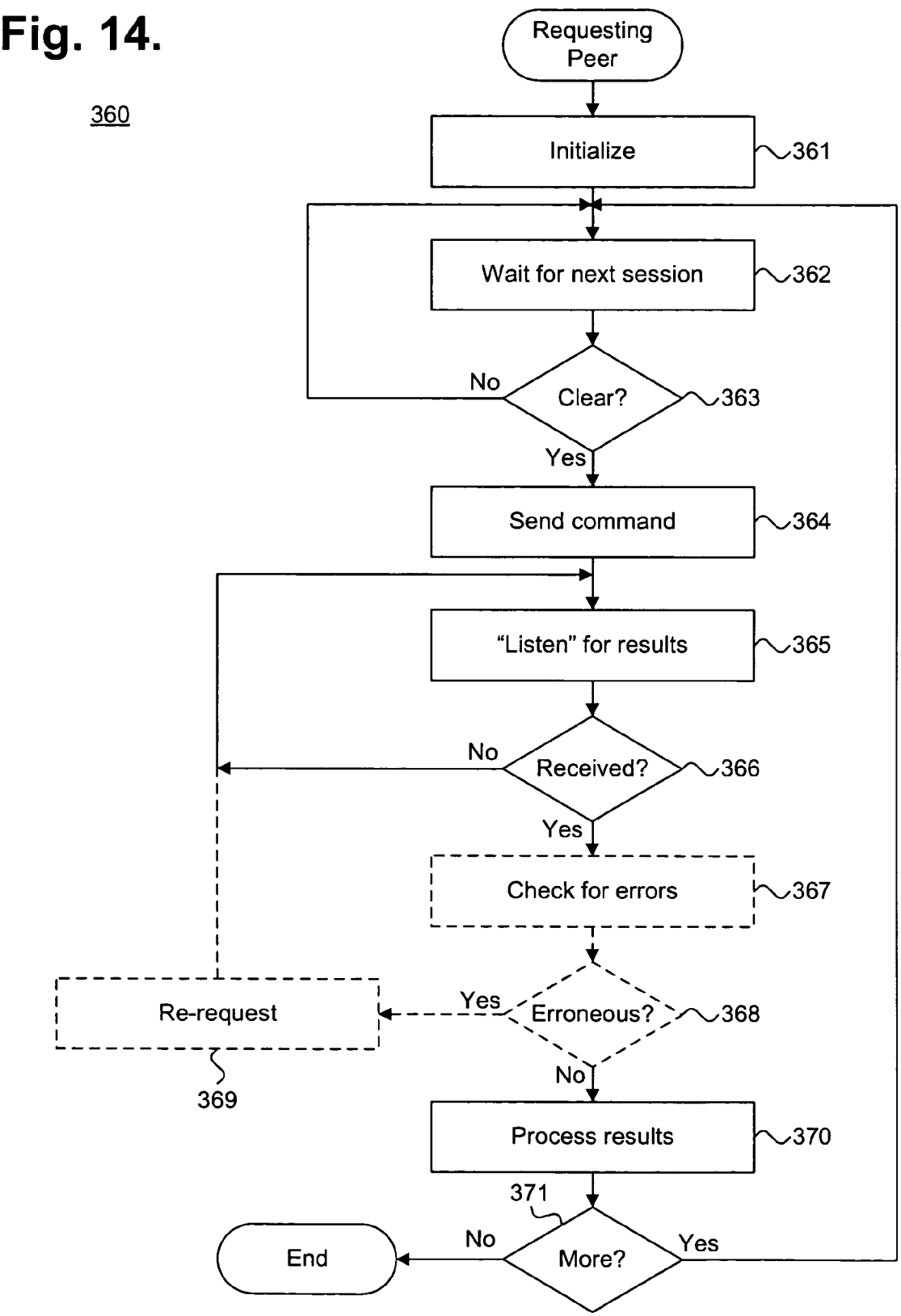
FIG. 14 is a flow diagram showing a method for providing digital data communications over a wireless intra-body network from a requesting peer, in accordance with an embodiment of the invention.

FIG. 14 is a flow diagram showing a method 360 for providing digital data communications over a wireless intra-body network 117 from a requesting peer 231, in accordance with an embodiment of the invention. In one embodiment, communications sessions are periodically self-initiated between the cooperating IMs 116a-d, which exchange command message requests and results through wireless data packets. In a further embodiment, the IMs 116a-d perform error control to ensure error-free transmissions. However, the data exchanged between the requesting IM 116a and the one or more responding IMs 116b-d need not be limited to a response-request format. In a further embodiment, commands can be sent bi-directionally between the requesting IM 116a and the one or more responding IMs 116b-d. Moreover, in a still further embodiment, commands are implied and only data is exchanged between the requesting IM 116a and the one or more responding IMs 116b-d following automatic command execution. The method 360 is described as a sequence of process operations or steps, which can be executed, for instance, by an IM 116a in a peer-to-peer network configuration.

Each requesting peer 231 begins by initializing (block 361), which can include performing authentication 233 (shown in FIG. 5). The requesting peer 231 is then ready to begin communications with one or more responding peer 232 (blocks 362-371). A communications session can be started by the requesting peer 231 at pre-determined times. After waiting for a pre-determined delay to begin the next communications session (block 362), the requesting peer 231 performs arbitration 236 by checking for a clear communications channel (block 363). If the communications channel is not clear (block 363), the requesting peer 231 continues waiting (block 362). Otherwise, the requesting peer 231 sends a command message (block 364) and "listens" for results (block 365) to be received back from the responding peer 232. If the results have not yet been received (block 366), the requesting peer 231 continues "listening" for results (block 365). Otherwise, in a further embodiment, the requesting peer 231 checks the results for errors (block 367). If errors are detected (block 368), the requesting peer 231 re-requests that the results be resent (block 369). Otherwise, the requesting peer 231 processes the results (block 370) and, if more communications sessions are required (block 371), the requesting peer 231 continues to wait for the next communications session (block 362). Otherwise, the method terminates.

Responding Peer Method Overview

Figure 15:
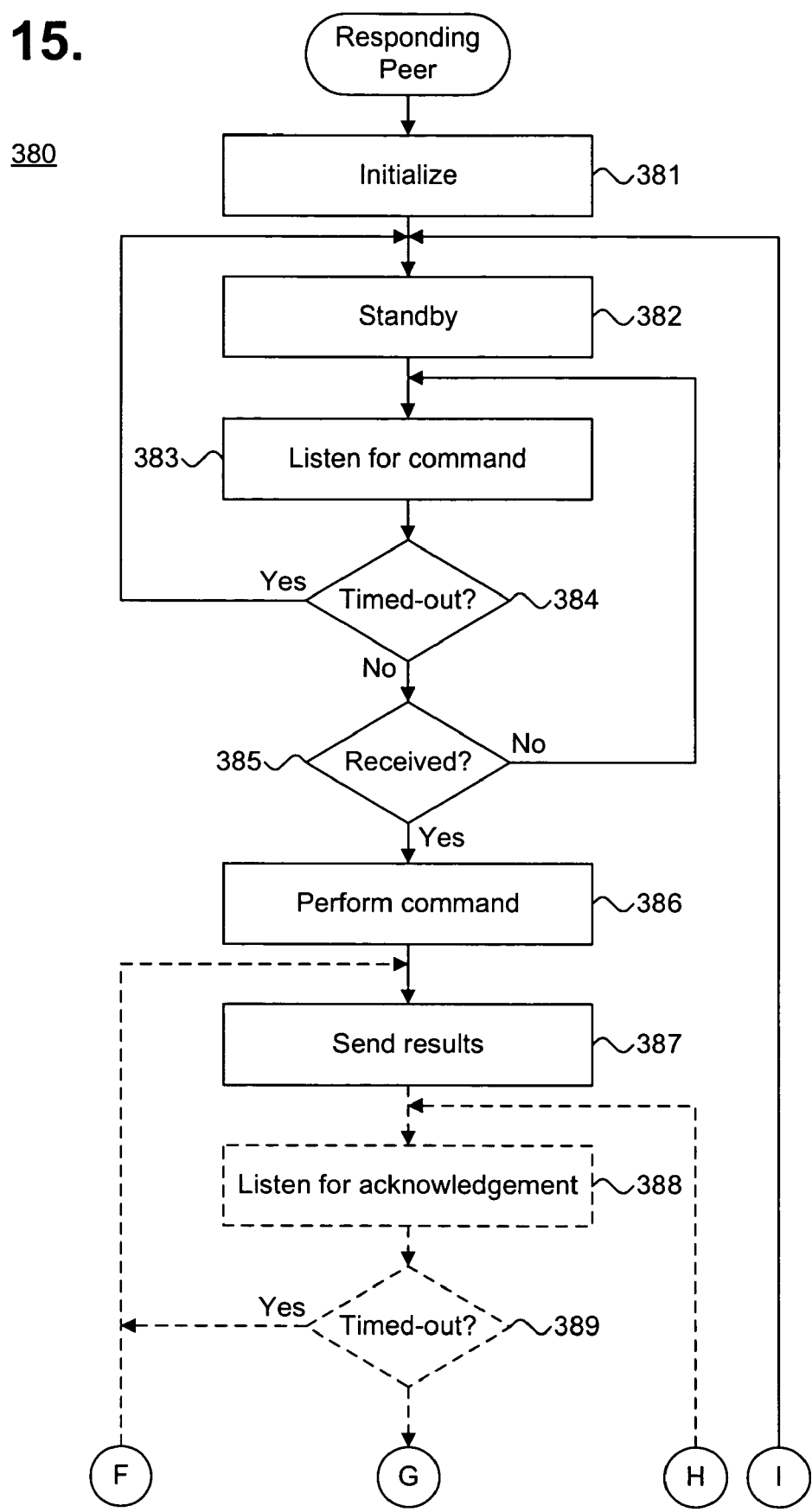
FIG. 15 is a flow diagram showing a method for providing digital data communications over a wireless intra-body network from a responding peer, in accordance with an embodiment of the invention.
Figure 15:
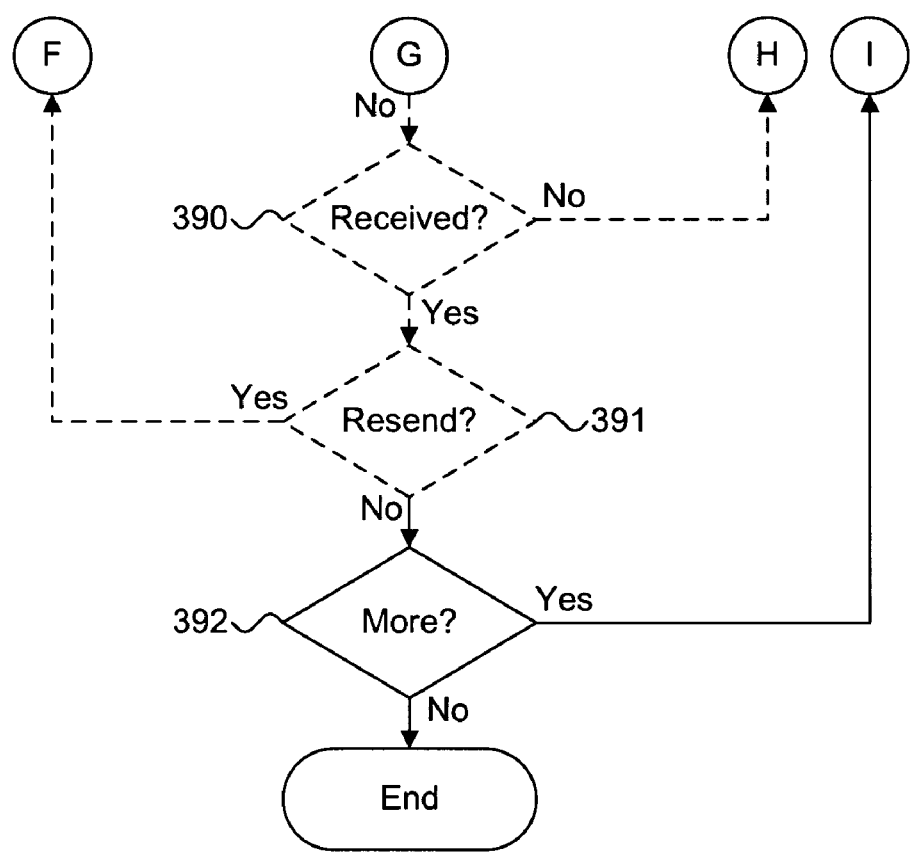

FIG. 15 is a flow diagram showing a method 380 for providing digital data communications over a wireless intra-body network 117 from a responding peer 232, in accordance with an embodiment of the invention. Although described below with reference to a response-request format, in a further embodiment, commands can be sent bi-directionally and, in a still further embodiment, commands are implied and only data is exchanged following automatic command execution. The method 380 is described as a sequence of process operations or steps, which can be executed, for instance, by an IM 116a in a peer-to-peer network configuration.

Each responding peer 232 begins by initializing (block 391), which can include performing authentication 233 (shown in FIG. 5). The responding peer 232 is then ready to begin communications with one or more requesting peers 231 (blocks 382-392). Each responding peer 232 remains in a low power receive standby mode for a pre-determined delay (block 382), after which the responding peer 232 awakens by switching to a high power receive mode and "listens" for a command message packet sent from the requesting peer 231 (block 383). If, after a predetermined delay, no command message packet has been received, the responding peer 232 times out (block 384) and returns to the standby mode (block 382). Otherwise, if a command message packet has not yet been received (block 385) and the responding peer 232 has not yet timed out (block 384), the responding peer 232 continues "listening" for an address packet (block 383).

If a command message packet has been received (block 385), the command message is performed (block 386), which, in one embodiment, can include performing one or more actions, such as monitoring or delivering therapy. Upon completion of the command message, the results of the command message are sent to the requesting peer 231 (block 387). Otherwise, in a further embodiment, the responding peer 232 "listens" for an acknowledgement while the requesting peer 231 checks the results for errors (block 388). If, after a pre-determined delay, no acknowledgement packet has been received, the responding peer 232 times out (block 389) and resends the results (block 387). Otherwise, if an acknowledgement packet has not yet been received (block 390) and the responding peer 232 has not yet timed out (block 389), the responding peer 232 continues "listening" for an acknowledgement packet (block 388). If errors are detected, the requesting peer 231 will re-requests that the results be resent (block 391). Otherwise, upon receiving an acknowledgement packet (block 390), if no request to resend the results has been sent by the requesting peer 231 (block 391), and, if more communications sessions are required (block 392), the responding peer 232 returns to the standby mode (block 382). Otherwise, the method terminates.

While the invention has been particularly shown and described as referenced to the embodiments thereof, those skilled in the art will understand that the foregoing and other changes in form and detail may be made therein without departing from the spirit and scope of the invention.

What is claimed is:

1. A system for providing digital data communications over a wireless intra-body network, comprising:
   a physical protocol layer logically defined in a plurality of implantable devices in an intra-body network with an identifier uniquely assigned to each such implantable device; and
   functions specified within the physical protocol layer to transact data exchange over a wireless interface, comprising:
      an activation state to activate a slave implantable device in response to an activation signal transmitted through the wireless interface by a master implantable device;
      an identification state to establish a wireless communications link between the slave implantable device and the master implantable device upon matching of the identifier assigned to the slave implantable device;
      an authentication state to mutually authenticate the slave implantable device and the master implantable device prior to initiating the wireless communications link;
      a command state to communicate data intra-bodily over the communications link; and
      an arbitration state for the purpose of preventing overlapping communication to arbitrate control of the communications link between master implantable devices participating in the intra-body network.

2. A system according to claim 1, further comprising:
   an error control state to implement error control over the data upon receipt by at least one of the slave implantable device and the master implantable device.

3. A system according to claim 2, wherein the error control is selected from the group comprising:
   an acknowledgement of acceptable data receipt;
   a cyclic redundancy code over the data;
   parity over the data; and
   a request for new data in lieu of the data received.

4. A system according to claim 1, wherein the master implantable device is activated in an active state to commence and complete the data exchange, and maintained in an off state absent the data exchange.

5. A system according to claim 1, wherein the slave implantable device is sustained in an active state during the data exchange, and maintained in a standby state absent the data exchange.

6. A system according to claim 5, wherein the slave implantable device is returned to the standby state upon at least one of an unsuccessful matching of the identifier assigned to the slave implantable device, timing out, command by the master implantable device and a termination of the data exchange.

7. A system according to claim 1, wherein the master implantable device comprises an implantable medical device performing at least one of an autonomous control, therapeutic and sensing function independent of any other such implantable device.

8. A system according to claim 1, wherein the slave implantable device comprises an implantable device performing at least one of an autonomous therapeutic and sensing function.

9. A system according to claim 1, wherein the wireless interface comprises at least one of an acoustic, optical, electronic field, and inductive interface.

10. A method for providing digital data communications over a wireless intra-body network, comprising:
   logically defining a physical protocol layer with an identifier uniquely assigned to a plurality of implantable devices in an intra-body network; and
   specifying functions within the physical protocol layer to transact data exchange over a wireless interface, comprising:
      activating a slave implantable device in response to an activation signal transmitted through the wireless interface by a master implantable device;
      establishing a wireless communications link between the slave implantable device and the master implantable device upon matching of the identifier assigned to the slave implantable device;
      mutually authenticating the slave implantable device and the master implantable device prior to initiating the wireless communications link;
      communicating data intra-bodily over the communications link; and
      arbitrating control of the communications link between master implantable devices participating in the intra-body network for the purpose of preventing overlapping communication.

11. A method according to claim 10, further comprising:
   implementing error control over the data upon receipt by at least one of the slave implantable device and the master implantable device.

12. A method according to claim 11, wherein the error control is selected from the group comprising:
   providing an acknowledgement of acceptable data receipt;
   determining a cyclic redundancy code over the data;
   determining parity over the data; and
   requesting new data in lieu of the data received.

13. A method according to claim 10, further comprising:
   activating the master implantable device in an active state to commence and complete the data exchange; and
   maintaining the master implantable device in an off state absent the data exchange.

14. A method according to claim 10, further comprising:
   sustaining the slave implantable device in an active state during the data exchange; and
   maintaining the slave implantable device in a standby state absent the data exchange.

15. A method according to claim 14, further comprising:
   returning the slave implantable device to the standby state upon at least one of an unsuccessful matching of the identifier assigned to the slave implantable device, timing out, command by the master implantable device and a termination of the data exchange.

16. A method according to claim 10, wherein the master implantable device comprises an implantable medical device performing at least one of an autonomous control, therapeutic and sensing function independent of any other such implantable device.

17. A method according to claim 10, wherein the slave implantable device comprises an implantable device performing at least one of an autonomous therapeutic and sensing function.

18. A method according to claim 10, wherein the wireless interface comprises at least one of an acoustic, optical, electronic field, and inductive interface.

19. A computer-readable storage medium storing code for providing digital data communications over a wireless intra-body network, comprising:
   code for logically defining a physical protocol layer with an identifier uniquely assigned to a plurality of implantable devices in an intra-body network; and
   code for specifying functions within the physical protocol layer to transact data exchange over a wireless interface, comprising:
      code for activating a slave implantable device in response to an activation signal transmitted through the wireless interface by a master implantable device;
      code for establishing a wireless communications link between the slave implantable device and the master implantable device upon matching of the identifier assigned to the slave implantable device;
      code for mutually authenticating the slave implantable device and the master implantable device prior to initiating the wireless communications link;
      code for communicating data intra-bodily over the communications link; and
      code for arbitrating control of the communications link between master implantable devices participating in the intra-body network for the purpose of preventing overlapping communication.

20. An apparatus for providing digital data communications over a wireless intra-body network, comprising:
   means for logically defining a physical protocol layer with an identifier uniquely assigned to a plurality of implantable devices in an intra-body network; and
   means for specifying functions within the physical protocol layer to transact data exchange over a wireless interface, comprising:
      means for activating a slave implantable device in response to an activation signal transmitted through the wireless interface by a master implantable device;
      means for establishing a wireless communications link between the slave implantable device and the master implantable device upon matching of the identifier assigned to the slave implantable device;
      means for mutually authenticating the slave implantable device and the master implantable device prior to initiating the wireless communications link;
      means for communicating data intra-bodily over the communications link; and
      means for arbitrating control of the communications link between master implantable devices participating in the intra-body network for the purpose of preventing overlapping communication.

21. A system for providing digital data communications over a wireless intra-body network, comprising:
   a physical protocol layer logically defined in a plurality of peer implantable devices in an intra-body network with an identifier uniquely assigned to each such peer implantable device; and
   functions specified within the physical protocol layer to transact data exchange over a wireless interface, comprising:
      an identification state to establish a wireless communications link between a responding peer implantable device and a requesting peer implantable device upon matching of the identifier assigned to the responding peer implantable device;
      an authentication state to mutually authenticate the responding peer implantable device and the requesting peer implantable device prior to initiating the wireless communications link;
      a command state to communicate data intra-bodily over the communications link; and
      an arbitration state for the purpose of preventing overlapping communication to arbitrate control of the communications link between the peer implantable devices participating in the intra-body network.

22. A system according to claim 21, further comprising:
   an error control state to implement error control over the data upon receipt by at least one of the responding peer implantable device and the requesting peer implantable device.

23. A system according to claim 22, wherein the error control is selected from the group comprising:
   an acknowledgement of acceptable data receipt;
   a cyclic redundancy code over the data;
   parity over the data; and
   a request for new data in lieu of the data received.

24. A system according to claim 21, wherein the requesting peer implantable device and the responding peer implantable device are activated in an active state to commence and complete the data exchange, and maintained in an off state absent the data exchange.

25. A system according to claim 21, wherein the requesting peer implantable device and the responding peer implantable device are sustained in an active state during the data exchange, and maintained in a standby state absent the data exchange.

26. A system according to claim 21, wherein the responding peer implantable device is returned to the standby state upon at least one of an unsuccessful matching of the identifier assigned to the responding peer implantable device, timing out, command by the requesting peer implantable device and a termination of the data exchange.

27. A system according to claim 21, wherein the responding peer implantable device comprises an implantable device performing at least one of an autonomous therapeutic and sensing function.

28. A system according to claim 21, wherein the wireless interface comprises at least one of an acoustic, optical, electronic field, and inductive interface.

29. A method for providing digital data communications over a wireless intra-body network, comprising:
   logically defining a physical protocol layer with an identifier uniquely assigned to a plurality of peer implantable devices in an intra-body network; and
   specifying functions within the physical protocol layer to transact data exchange over a wireless interface, comprising:
      establishing a wireless communications link between a responding peer implantable device and a requesting peer implantable device upon matching of the identifier assigned to the responding peer implantable device;
      mutually authenticating the responding peer implantable device and the requesting peer implantable device prior to initiating the wireless communications link;
      communicating data intra-bodily over the communications link; and
      arbitrating control of the communications link between the peer implantable devices participating in the intra-body network for the purpose of preventing overlapping communication.

30. A method according to claim 29, further comprising:
   implementing error control over the data upon receipt by at least one of the responding peer implantable device and the requesting peer implantable device.

31. A method according to claim 30, wherein the error control is selected from the group comprising:
   providing an acknowledgement of acceptable data receipt;
   determining a cyclic redundancy code over the data;
   determining parity over the data; and
   requesting new data in lieu of the data received.

32. A method according to claim 29, further comprising:
   sustaining the requesting peer implantable device and the responding peer implantable device in an active state during the data exchange; and
   maintaining the requesting peer implantable device and the responding peer implantable device in a standby state absent the data exchange.

33. A method according to claim 29, further comprising:
   returning the requesting peer implantable device and the responding peer implantable device to the standby state upon at least one of an unsuccessful matching of the identifier assigned to the responding peer implantable device, timing out, command by the requesting peer implantable device and a termination of the data exchange.

34. A method according to claim 29, wherein the responding peer implantable device comprises an implantable device performing at least one of an autonomous therapeutic and sensing function.

35. A method according to claim 29, wherein the wireless interface comprises at least one of an acoustic, optical, electronic field, and inductive interface.

36. A computer-readable storage medium storing code for providing digital data communications over a wireless intra-body network, comprising:
   code for logically defining a physical protocol layer with an identifier uniquely assigned to a plurality of peer implantable devices in an intra-body network; and
   code for specifying functions within the physical protocol layer to transact data exchange over a wireless interface, comprising:
      code for establishing a wireless communications link between a responding peer implantable device and a requesting peer implantable device upon matching of the identifier assigned to the responding peer implantable device;

code for mutually authenticating the responding peer implantable device and the requesting peer implantable device prior to initiating the wireless communications link;

code for communicating data intra-bodily over the communications link; and code for arbitrating control of the communications link between the peer implantable devices participating in the intra-body network for the purpose of preventing overlapping communication.

37. An apparatus for providing digital data communications over a wireless intra-body network, comprising:

means for logically defining a physical protocol layer with an identifier uniquely assigned to a plurality of peer implantable devices in an intra-body network; and means for specifying functions within the physical protocol layer to transact data exchange over a wireless interface, comprising:

means for establishing a wireless communications link between a responding peer implantable device and a requesting peer implantable device upon matching of the identifier assigned to the responding peer implantable device;

means for mutually authenticating the responding peer implantable device and the requesting peer implantable device prior to initiating the wireless communications link;

means for communicating data intra-bodily over the communications link; and means for arbitrating control of the communications link between the peer implantable devices participating in the intra-body network for the purpose of preventing overlapping communication.

38. A system for providing digital data communications over a wireless intra-body network, comprising:

a physical protocol layer logically defined in a plurality of implantable devices in an intra-body network and in a device external to the intra-body network with an identifier uniquely assigned to the implantable devices and the external device; and functions specified within the physical protocol layer to transact data exchange over a wireless interface, comprising:

an activation state to activate an implantable device in response to an activation signal transmitted through the wireless interface by the external device;

an identification state to establish a wireless communications link between the implantable device and the external device upon matching of the identifier assigned to the implantable device;

an authentication state to mutually authenticate the implantable device and the external device prior to initiating the wireless communications link; and a command state to communicate data intra-bodily over the communications link; and functions specified within each of the implantable devices to arbitrate control of the communications between each such other implantable device participating in the intra-body network for the purpose of preventing overlapping communication.

39. A system according to claim 38, wherein the external device comprises at least one of a repeater, programmer, and dedicated recharger.

40. A system according to claim 38, wherein the wireless interface comprises at least one of an acoustic, optical, electronic field, and inductive interface.

41. A method for providing digital data communications over a wireless intra-body network, comprising:

logically defining a physical protocol layer with an identifier uniquely assigned to a plurality of implantable devices in an intra-body network and an identifier uniquely assigned to a device external to the intra-body network; and specifying functions within the physical protocol layer to transact data exchange over a wireless interface, comprising:

activating an implantable device in response to an activation signal transmitted through the wireless interface by the external device;

establishing wireless communications link between the implantable device and the external device upon matching of the identifier assigned to the implantable device;

mutually authenticating the implantable device and the external device prior to initiating the wireless communications link; and communicating data intra-bodily over the communications link; and specifying functions within each of the implantable devices to arbitrate control of the communications between each such other implantable device participating in the intra-body network for the purpose of preventing overlapping communication.

42. A method according to claim 41, wherein the external device comprises at least one of a repeater, programmer, and dedicated recharger.

43. A method according to claim 41, wherein the wireless interface comprises at least one of an acoustic, optical, electronic field, and inductive interface.

44. A computer-readable storage medium storing code for providing digital data communications over a wireless intra-body network, comprising:

code for logically defining a physical protocol layer with an identifier uniquely assigned to a plurality of implantable devices in an intra-body network and an identifier uniquely assigned to a device external to the intra-body network; and code for specifying functions within the physical protocol layer to transact data exchange over a wireless interface, comprising:

code for activating an implantable device in response to an activation signal transmitted through the wireless interface by the external device;

code for establishing wireless communications link between the implantable device and the external device upon matching of the identifier assigned to the implantable device;

code for mutually authenticating the implantable device and the external device prior to initiating the wireless communications link; and code for communicating data intra-bodily over the communications link; and code for specifying functions within each of the implantable devices to arbitrate control of the communications between each such other implantable device participating in the intra-body network for the purpose of preventing overlapping communication.

45. An apparatus for providing digital data communications over a wireless intra-body network, comprising:

means for logically defining a physical protocol layer with an identifier uniquely assigned to a plurality of implantable devices in an intra-body network and an identifier uniquely assigned to a device external to the intra-body network; and means for specifying functions within the physical protocol layer to transact data exchange over a wireless interface, comprising:

means for activating an implantable device in response to an activation signal transmitted through the wireless interface by the external device;

means for establishing a wireless communications link between the implantable device and the external device upon matching of the identifier assigned to the implantable device;

means for mutually authenticating the implantable device and the external device prior to initiating the wireless communications link; and means for communicating data intra-bodily over the communications link; and means for specifying functions within each of the implantable devices to arbitrate control of the communications between each such other implantable device participating in the intra-body network for the purpose of preventing overlapping communication.

\* \* \* \* \*